(12) United States Patent
Gysling

(10) Patent No.: US 8,061,186 B2
(45) Date of Patent: Nov. 22, 2011

(54) SYSTEM AND METHOD FOR PROVIDING A COMPOSITIONAL MEASUREMENT OF A MIXTURE HAVING ENTRAINED GAS

(75) Inventor: Daniel L. Gysling, Glastonbury, CT (US)

(73) Assignee: Expro Meters, Inc., Wallingford, CT (US)

( * ) Notice: Subject to any disclaimer, the term of this patent is extended or adjusted under 35 U.S.C. 154(b) by 635 days.

(21) Appl. No.: 12/055,566

(22) Filed: Mar. 26, 2008

(65) Prior Publication Data

US 2009/0241672 A1    Oct. 1, 2009

(51) Int. Cl.
*G01N 30/90* (2006.01)

(52) U.S. Cl. ............................................ 73/61.54

(58) Field of Classification Search ............ 73/61.54, 73/61.45, 597, 861.25, 861.27
See application file for complete search history.

(56) References Cited

U.S. PATENT DOCUMENTS

| | | | |
|---|---|---|---|
| 2,874,568 A | 2/1959 | Petermann | 73/861.02 |
| 3,751,979 A | 8/1973 | Ims | 73/861.27 |
| 4,048,853 A | 9/1977 | Smith et al. | 73/861.25 |
| 4,262,523 A | 4/1981 | Stansfeld | 73/24.05 |
| 4,320,659 A | 3/1982 | Lynnworth et al. | 73/589 |
| 4,580,444 A | 4/1986 | Abts et al. | 73/61.75 |
| 4,628,725 A | 12/1986 | Gouilloud et al. | 73/19.03 |
| 4,773,257 A | 9/1988 | Aslesen et al. | 73/61.44 |
| 4,852,068 A | 7/1989 | Track | 367/57 |
| 4,862,060 A | 8/1989 | Scott et al. | 324/639 |
| 4,902,961 A | 2/1990 | De et al. | 324/640 |
| 5,049,823 A | 9/1991 | Castel et al. | 324/640 |
| 5,083,452 A | 1/1992 | Hope | 73/61.49 |
| 5,101,163 A | 3/1992 | Agar | 324/639 |
| 5,131,279 A | 7/1992 | Lang et al. | |
| 5,148,405 A * | 9/1992 | Belchamber et al. | 367/13 |
| 5,224,372 A | 7/1993 | Kolpak | 73/19.03 |
| 5,259,239 A | 11/1993 | Gaisford | 73/61.44 |
| 5,285,675 A | 2/1994 | Colgate et al. | 73/23.2 |
| 5,287,752 A | 2/1994 | Den Boer | 73/861.04 |
| 5,359,897 A | 11/1994 | Hamstead et al. | 73/597 |
| 5,367,911 A | 11/1994 | Jewell et al. | 73/861.08 |
| 5,524,475 A | 6/1996 | Kolpak et al. | 73/19.03 |
| 5,591,922 A | 1/1997 | Segeral et al. | 73/861.04 |
| 5,594,180 A | 1/1997 | Carpenter et al. | 73/861.356 |

(Continued)

FOREIGN PATENT DOCUMENTS

DE    4306119    9/1994

(Continued)

*Primary Examiner* — Hezron E Williams
*Assistant Examiner* — Tamiko Bellamy
(74) *Attorney, Agent, or Firm* — O'Shea Getz P.C.

(57) ABSTRACT

A method and apparatus for determining at least one characteristic of a fluid flowing within a pipe is provided. The fluid flow may include one or more liquid component bodies and one or more gas component bodies, which bodies occupy a substantial cross-sectional area of the pipe when passing a location in the pipe. The method includes, and the apparatus includes elements operable to perform, the steps of: 1) transmitting a signal into the fluid flow at the location within the pipe, and receiving the signal after it has traversed at least a portion of the fluid flow; 2) determining a time of flight of the signal traversing the fluid flow; 3) determining the presence of a liquid component body at the location in the pipe, using the determined time of flight; and 4) determining at least one characteristic of the fluid using fluid data generated if the liquid component body is present at the location.

30 Claims, 17 Drawing Sheets

U.S. PATENT DOCUMENTS

| | | | |
|---|---|---|---|
| 5,654,551 A | 8/1997 | Watt et al. | 250/356.1 |
| 5,708,211 A | 1/1998 | Jepson et al. | 73/861.04 |
| 5,770,806 A | 6/1998 | Hiismaki | 73/861.29 |
| 5,835,884 A | 11/1998 | Brown | 702/45 |
| 6,016,702 A | 1/2000 | Maron | 73/705 |
| 6,354,147 B1 | 3/2002 | Gysling et al. | 73/61.79 |
| 6,442,996 B1 | 9/2002 | Thurston et al. | 73/24.01 |
| 6,443,226 B1 | 9/2002 | Diener et al. | 166/241.6 |
| 6,450,037 B1 | 9/2002 | McGuinn et al. | 73/705 |
| 6,463,813 B1 | 10/2002 | Gysling | 73/862.59 |
| 6,481,288 B1 | 11/2002 | Humphrey et al. | 73/597 |
| 6,502,465 B1 | 1/2003 | Vedapuri et al. | 73/861.04 |
| 6,550,342 B2 | 4/2003 | Croteau et al. | 73/800 |
| 6,550,345 B1 * | 4/2003 | Letton | 73/861.27 |
| 6,575,043 B1 | 6/2003 | Huang et al. | 73/861.25 |
| 6,587,798 B2 | 7/2003 | Kersey et al. | 702/50 |
| 6,609,069 B2 | 8/2003 | Gysling | 702/48 |
| 6,634,239 B2 | 10/2003 | Gomm | 73/861.27 |
| 6,686,737 B2 | 2/2004 | Kruspe et al. | 324/303 |
| 6,691,584 B2 | 2/2004 | Gysling et al. | 73/861.42 |
| 6,732,575 B2 | 5/2004 | Gysling et al. | 73/61.79 |
| 6,732,595 B2 | 5/2004 | Lynnworth | 73/861.27 |
| 6,745,135 B2 | 6/2004 | Keilty et al. | 702/45 |
| 6,763,698 B2 | 7/2004 | Greenwood | 73/30.01 |
| 6,782,150 B2 | 8/2004 | Davis | 385/12 |
| 6,813,962 B2 | 11/2004 | Gysling et al. | 73/861.26 |
| 6,837,098 B2 | 1/2005 | Gysling et al. | 73/61.79 |
| 6,862,920 B2 | 3/2005 | Gysling et al. | 73/61.79 |
| 6,889,562 B2 | 5/2005 | Gysling et al. | 73/861.42 |
| 6,945,095 B2 | 9/2005 | Johansen | 73/61.45 |
| 6,959,604 B2 | 11/2005 | Bryant et al. | 73/705 |
| 6,988,411 B2 | 1/2006 | Gysling et al. | 73/645 |
| 7,000,485 B2 | 2/2006 | Ao et al. | 73/861.29 |
| 7,028,538 B2 | 4/2006 | Gysling et al. | 73/61.75 |
| 7,032,432 B2 | 4/2006 | Gysling | 73/24.01 |
| 7,058,549 B2 | 6/2006 | Gysling | 702/189 |
| 7,059,172 B2 | 6/2006 | Gysling | 73/32 A |
| 7,062,976 B2 | 6/2006 | Gysling et al. | 73/861.18 |
| 7,096,719 B2 | 8/2006 | Gysling | 73/61.75 |
| 7,121,152 B2 | 10/2006 | Winston et al. | 73/861.42 |
| 7,127,360 B2 | 10/2006 | Gysling et al. | 702/45 |
| 7,134,320 B2 | 11/2006 | Gysling et al. | 73/32 A |
| 7,146,864 B2 | 12/2006 | Sullivan et al. | 73/861.42 |
| 7,153,003 B2 | 12/2006 | Nakamura | 362/353 |
| 7,181,955 B2 | 2/2007 | Gysling | 73/53.03 |
| 7,188,534 B2 | 3/2007 | Tombs et al. | 73/861.356 |
| 7,197,942 B2 | 4/2007 | Gysling et al. | 73/861.23 |
| 7,228,740 B2 | 6/2007 | Sinha | 73/579 |
| 7,237,440 B2 | 7/2007 | Gysling et al. | 73/861 |
| 7,293,471 B2 | 11/2007 | Lund Bo et al. | 73/861.52 |
| 7,295,933 B2 | 11/2007 | Gysling et al. | 702/45 |
| 7,322,251 B2 | 1/2008 | Gysling et al. | 73/861.26 |
| 7,330,797 B2 | 2/2008 | Bailey et al. | 702/50 |
| 7,331,233 B2 | 2/2008 | Scott | 73/596 |
| 7,359,803 B2 | 4/2008 | Gysling et al. | 702/25 |
| 7,363,800 B2 | 4/2008 | Gysling | 73/19.01 |
| 7,380,439 B2 | 6/2008 | Gysling et al. | 73/32 A |
| 7,389,187 B2 | 6/2008 | Kersey et al. | 702/45 |
| 7,400,985 B2 | 7/2008 | Fernald et al. | 702/48 |
| 7,430,924 B2 | 10/2008 | Gysling et al. | 73/861 |
| 7,434,621 B2 | 10/2008 | Aarvik et al. | 166/267 |
| 7,437,946 B2 | 10/2008 | Gysling | 73/861.23 |
| 7,454,981 B2 | 11/2008 | Gysling | 73/861.31 |
| 7,526,966 B2 | 5/2009 | Gysling et al. | 73/861.23 |
| 2004/0194539 A1 | 10/2004 | Gysling | |
| 2005/0050956 A1 | 3/2005 | Gysling et al. | 73/753 |
| 2005/0061060 A1 | 3/2005 | Gysling et al. | |
| 2007/0001028 A1 * | 1/2007 | Gysling | 239/318 |
| 2007/0006640 A1 * | 1/2007 | Gysling | 73/61.44 |
| 2007/0055464 A1 | 3/2007 | Gysling | 702/50 |
| 2007/0286136 A1 | 12/2007 | Rittle et al. | 370/338 |
| 2008/0098818 A1 | 5/2008 | Fernald et al. | 73/622 |
| 2008/0098824 A1 | 5/2008 | Bailey et al. | 73/861.27 |
| 2008/0173100 A1 | 7/2008 | Davis | 73/861.27 |
| 2009/0025487 A1 | 1/2009 | Gysling et al. | 73/861.25 |
| 2009/0158858 A1 | 6/2009 | Gysling et al. | 73/861.27 |
| 2009/0229364 A1 | 9/2009 | Gysling | 73/623 |

FOREIGN PATENT DOCUMENTS

| | | |
|---|---|---|
| EP | 222503 | 5/1987 |
| EP | 253504 | 1/1988 |
| GB | 2282931 | 4/1995 |
| WO | 93/14382 | 7/1993 |

* cited by examiner

FIG. 15
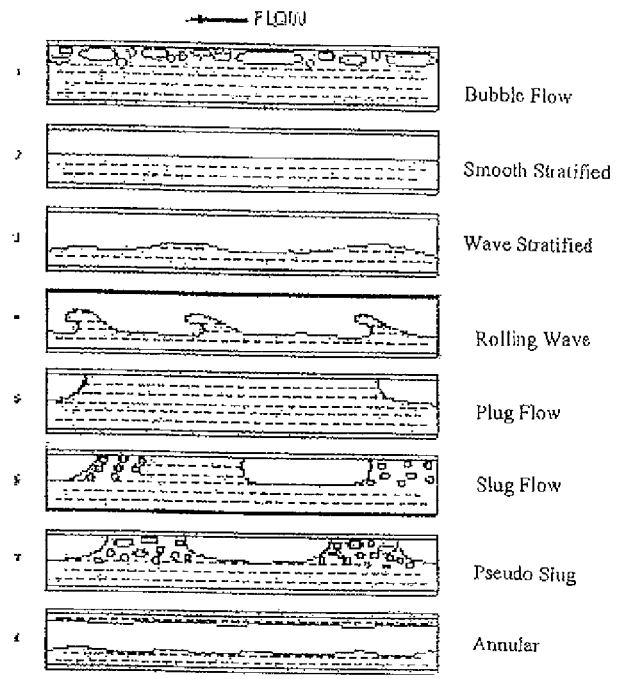
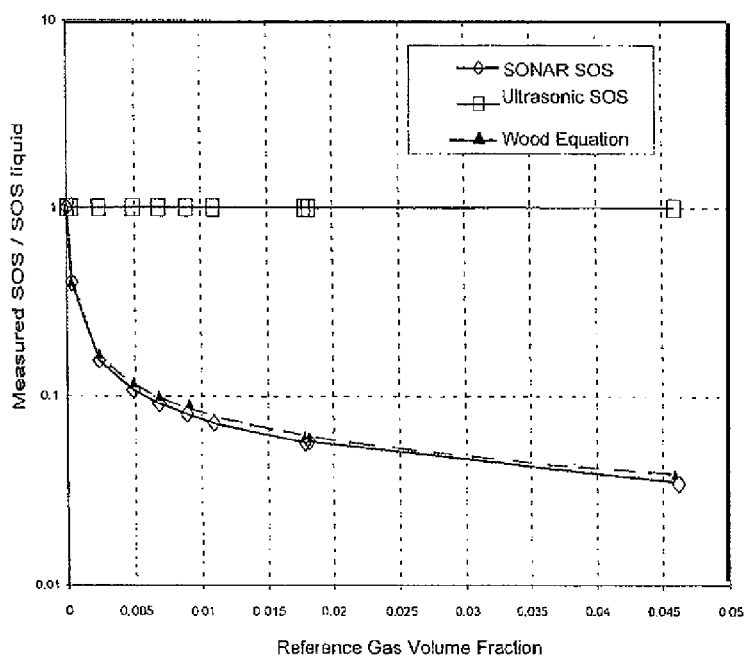
FIG. 16

FIG. 17
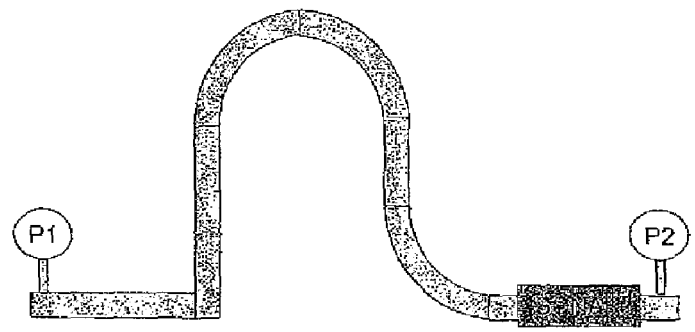
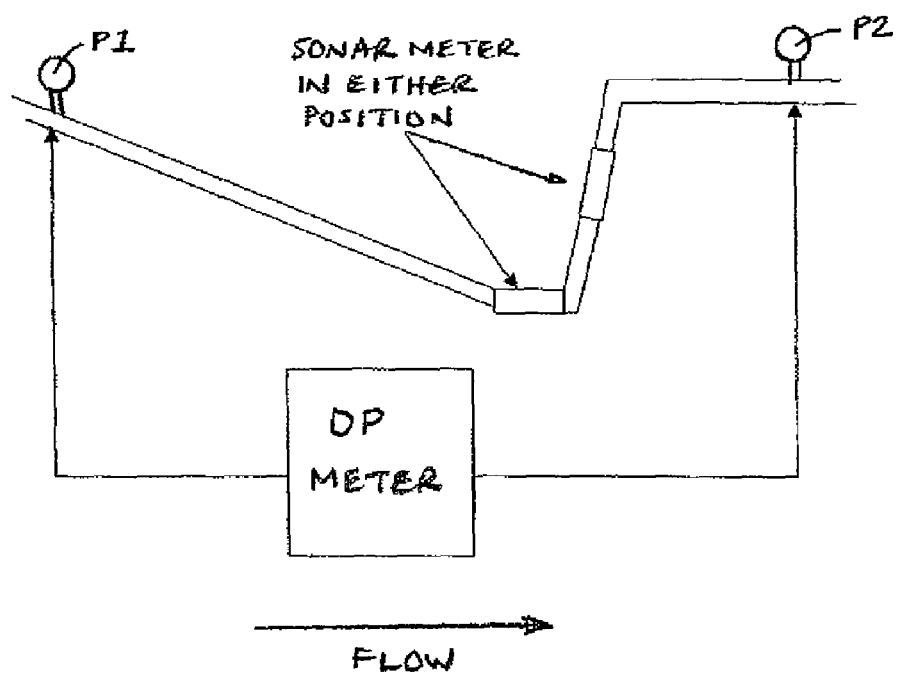

SYSTEM AND METHOD FOR PROVIDING A COMPOSITIONAL MEASUREMENT OF A MIXTURE HAVING ENTRAINED GAS

BACKGROUND OF THE INVENTION

1. Technical Field

This invention relates generally to a system for measuring the composition, velocity and volumetric flow rate of each phase of a multi-phase mixture (e.g., oil, water, and gas mixture) having entrained gas therein, and more particularly to a system that measures the speed of sound propagating through a flow to determine compositional measurements compensated for entrained gas.

2. Background Information

Currently, there is an unmet need for multiphase flow measurement in oil and gas production. In fact, the accurate monitoring of well head production rates in the presence of entrained gas has long presented a difficult technical challenge to the oil and gas industry. Performing accurate and timely monitoring of the production rates has many benefits, including the optimization of overall field production and specific well production. The difficulty is due in no small part to the extreme variability of produced fluids which can include various types and mixtures of oil, water, gas, and solid particles.

In response to the above discussed issues, many companies have developed various types of three phase meters that are designed to address the well head flow metering market. However, these products have met relatively limited commercial success due to a combination of performance, accuracy, and cost issues. In light of this, the present invention provides a means and apparatus for well head monitoring that combines multiple existing technologies to meet a wide range of cost and performance goals.

Another difficulty with measuring the composition of the oil/water mixture at the well head involves the pipe not being continuously filled during the pumping processes. In other words, the gas void fraction may randomly vary from 0% to 50%. Unfortunately, current apparatus for measuring the gas void fraction has difficulty or may not be able to accurately measure the gas void fraction of the oil and gas mixture. The present invention provides a continuous real-time measurement of the oil and water mixture having entrained air that temporally varies as the mixture flows through the pipe.

"Slugging" is a common phenomenon in the transport of gas/liquid mixtures, wherein liquid component bodies (i.e., "slugs") are dispersed within a gas/liquid flow. A slug is present within a pipe at a given location when the liquid component body fills substantially all of the cross-sectional area of the pipe at the location. The slug may consist of a single component (i.e., water or liquid hydrocarbon) or a mixture of components (e.g., a mixture of water and liquid hydrocarbon). A slug may include some amount of entrained gases, which entrained gases are distinguishable from gas component bodies within the flow by virtue of the amount of gas present. A liquid slug and a gas component body cannot both be present at a particular location in the pipe at the same time. Naturally occurring slugs vary in length, speed, duration and quality. The transient nature of the presence of slugs, and therefore the transient nature of the liquid continuous conditions, makes it desirable to identify the fluid sound speed as quickly and accurately as possible.

The dynamics of gas/liquid flows can be very complicated. FIG. 15 schematically illustrates some of the more commonly occurring types of flow regimes that may be found in horizontal fluid flows. Gas/liquid flows can take many forms, however, and are therefore not limited to these illustrative flow regime examples. The term "horizontal" as used herein is defined as a direction that is substantially perpendicular to the local gravity vector.

What is needed is a system and method for determining at least one characteristic of a fluid flowing within a pipe, one that can accommodate a variety of fluid flows within a pipe, which flow may include one or more gas component bodies and one or more liquid component bodies.

SUMMARY OF THE INVENTION

According to the present invention, a method for determining at least one characteristic of a fluid flowing within a pipe is provided. The fluid flow may include one or more liquid component bodies and one or more gas component bodies, which bodies occupy a substantial cross-sectional area of the pipe when passing a location in the pipe. The method includes the steps of: 1) transmitting a signal into the fluid flow at the location within the pipe, and receiving the signal after it has traversed at least a portion of the fluid flow; 2) determining a time of flight of the signal traversing the fluid flow; 3) determining the presence of a liquid component body at the location in the pipe, using the determined time of flight; and 4) determining at least one characteristic of the fluid using fluid data generated if the liquid component body is present at the location.

According to an aspect of the present invention, an apparatus for determining at least one characteristic of a fluid flowing within a pipe is provided. Here again, the fluid may include one or more liquid component bodies and one or more gas component bodies, which bodies occupy a substantial cross-sectional area of the pipe when passing a location in the pipe. The apparatus includes a sensor and a processing device. The sensor includes a transmitter and a receiver, and is operable to send a signal into the fluid flow at the location within the pipe, receive the signal after it has traversed at least a portion of the fluid flow, and produce sensor data representative of the signal received. The processing device is in communication with the sensor. The processing device is operable to determine a time of flight of the signal traversing the fluid using the sensor data and determine a presence of a liquid component body at the location in the pipe using the determined time of flight. The processing device is further operable to determine at least one characteristic of the fluid if the presence of a liquid component body at the location is determined.

One of the advantages provided by the present system and method is that it provides a means by which to leverage the high variability exhibited in the transport of gas/liquid mixtures to determine a measure of the composition of the liquid component within the gas/liquid mixture.

The foregoing and other objects, features and advantages of the present invention will become more apparent in light of the following drawings and detailed description of the present invention.

BRIEF DESCRIPTION OF THE DRAWINGS

Referring now to the drawings, the foregoing and other features and advantages of the present invention will be more fully understood from the following detailed description of illustrative embodiments, taken in conjunction with the accompanying drawings in which like elements are numbered alike.

FIG. 15 is a schematic diagram illustrating examples of flow regimes for horizontal flow.

FIG. 16 is a graph of Measured SOS/SOS liquid versus Reference Gas Volume Fraction, illustrating the impact of entrained gases on measurements using passive SONAR and using ultrasonic sensors.

FIG. 17 is a schematic diagram illustrating a piping configuration operable to facilitate slug formation within a process flow.

FIG. 18 is a schematic diagram illustrating a piping configuration operable to facilitate slug formation within a process flow.

DETAILED DESCRIPTION OF THE INVENTION

Figure 1:
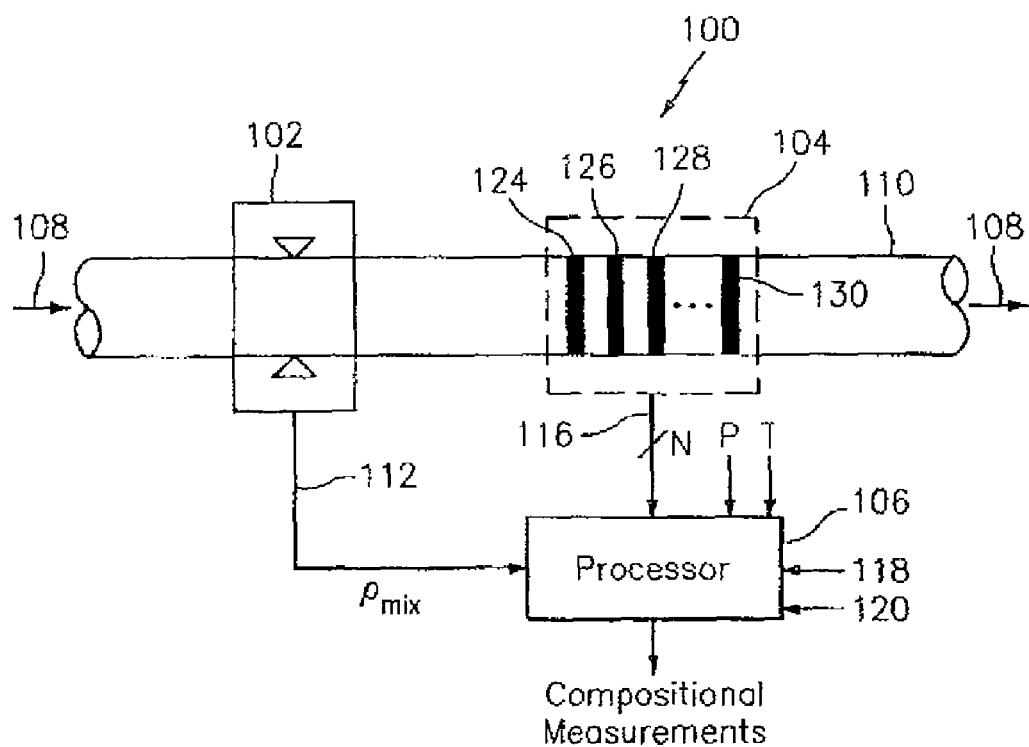
FIG. 1 is a schematic illustration of a flow measuring system for providing a density, composition, velocity and/or volumetric flow rate of the mixture in accordance with the present invention.

As is known, oil wells tend to produce widely varying amounts of oil, water and gas and thus, exhibit a wide range of multiphase flow patterns. As discussed hereinbefore, this is undesirable due to its negative impact on the measuring devices used to measure the components of a flow. As a result, economical, accurate, real-time measurement of individual well production has remained a long-standing challenge for the oil and gas industry. In order to obtain more accurate measurements, current methods typically involve some form of separation of the produced fluid prior to measurement. For example, producers have historically relied on three phase separators to divide the production streams into single-phase oil, water and gas streams for measurement using conventional, single-phase flow meters. Although generally effective, three phase separators have several undesirable properties that have driven the industry to seek alternative solutions, including size, cost and limited turndown ratios. Recently, advancement of online water cut and gas/liquid separation technology has enabled the industry to consider compact approaches based on two-phase separation. In these systems, the produced stream is separated into a gas and liquid stream for measurement and the net oil is determined by measuring the liquid rate and water cut of the liquid leg.

Although the accuracy of all separation-based measurement approaches is, to some degree, dependent upon separator effectiveness, the accuracy of a net oil measurement from a two-phase separation approach can be particularly sensitive to the presence of a small, but unknown amount of gas in the liquid leg due to its determination of the water cut of the liquid. In fact, from a volumetric flow perspective, the presence of entrained gases in the liquid stream will typically result in an over reporting of the volumetric flow of the liquid that is proportional to the amount of entrained (free) gas in the mixture and for most water cut devices, even a small amount of gas can result in a significant over reporting of oil content, and, in turn, a significant over reporting of net oil production. The sensitivity of the net oil measurement to gas carry-under is a function of the type of water cut monitoring device, as well as the properties of the produced fluids.

For example using a Coriolis-based density meter to the determine water cut of a mixture with entrained gas present results in the measured mixture density being less than the actual liquid density. Therefore, without knowledge of the presence of the gas, the water cut will be under-reported and net oil rate overstated. Similar inaccuracies will exist in all methods of microwave and nuclear density watercut measurement as well. If, however, the amount of gas in the liquid stream is accurately determined the liquid density can be calculated from the measured mixture density resulting in the proper watercut. Similar calculations can be made with microwave technology measurements. A gas void fraction meter, such as that manufactured by CiDRA Corporation, provides an accurate measurement of gas void fraction in a flowing liquid stream by measuring the propagation speed of naturally occurring low-frequency sound through the liquid/ gas mixture, wherein the GVF meter may be used in conjunction with a coriolis or microwave meter to provide the means to accurately measure the watercut in liquid streams independent of gas carry-under, as shown in FIGS. 1, 2, 3a and 3b.

Density meters provide a measurement of the density of a fluid flow or mixture passing through a pipe. As described in detail hereinbefore, a density meter typically provides erroneous density and composition measurements in the presence of entrained gas (e.g., randomly dispersed gas bubbles) within the fluid flow. It should be appreciated that the present invention provides composition measurements of a multiphase fluid having entrained gas, wherein the composition measurements include phase fraction of the phase of the mixture, volumetric flow of each phase of mixture, the oil cut, water cut and volumetric flow of mixture.

Moreover, it should be appreciated that one embodiment of the present invention proposes the use of sonar-based entrained gas measurements to determine the entrained gas level in conjunction with any density measurement of a mixture flowing in a pipe to make multiphase compositional measurements of the fluid. A sound speed based entrained gas measurement can accurately determine the amount of entrained gas in an aerated mixture without precise knowledge of the composition of either the non-gas components or the multiphase mixture or the composition of the gas itself. Thus, the entrained gas levels can be determined essentially independent of the determination of the liquid properties and, although not required, the accuracy could be improved by using the sound speed measurement and mixture density simultaneously. It should also be appreciated that determining the entrained gas level enables the density measurement to be used to determine the properties of the non-gas component of the multiphase mixture with the same precision as if the gas was not present. This capability also enables the density meters to provide significantly enhanced compositional information for aerated mixtures.

Referring to FIGS. 1-3b, one embodiment of a flow measuring system 100, in accordance with the present invention, is shown and includes a density meter 102, a sonar meter 104 (wherein the sonar meter 104 can measure the flow rate, the GVF and the SOS propagating through the fluid) and a processing unit 106 to provide any one or more of the following parameters of a fluid flow 108 flowing in a pipe 110, namely, mixture velocity, phase fraction of each phase (e.g., water, oil, and gas), volumetric flow rate of the mixture, and/or volumetric flow rate of each phase and mixture. The fluid flow 108 may be any aerated fluid and/or mixture including liquid, slurries, solid/liquid mixture, liquid/liquid mixture, solid/solid mixture and/or any other multiphase flow having entrained gas and/or water cut and oil cut. It should be appreciated that the sonar meter 104 may be any meter suitable to the desired purpose, such as dual function meter at that disclosed in U.S. patent application Ser. No. 10/875,857, filed Jun. 24, 2004, which is incorporated herein by reference in its entirety.

As will be described in greater detail hereinafter, the density meter 102 in combination with a sonar meter 104 can be used to determine the volumetric flow rates and composition of the mixture 108, namely gas void fraction. The limitation of this embodiment occurs when the gas void fraction is too great. For example, when the gas void fraction exceeds a predetermined value, the sonar meter 104 is unable to determine the gas void fraction. For flows that fill the pipe 110 but that have a gas void fraction that is below a predetermined value, the system 100 is able to determine the composition and volumetric flow parameters in accordance with the method described hereinafter, and also described in U.S. Pat. Nos. 7,127,360 and 7,134,320, which are incorporated herein by reference in their entireties.

Figure 2:
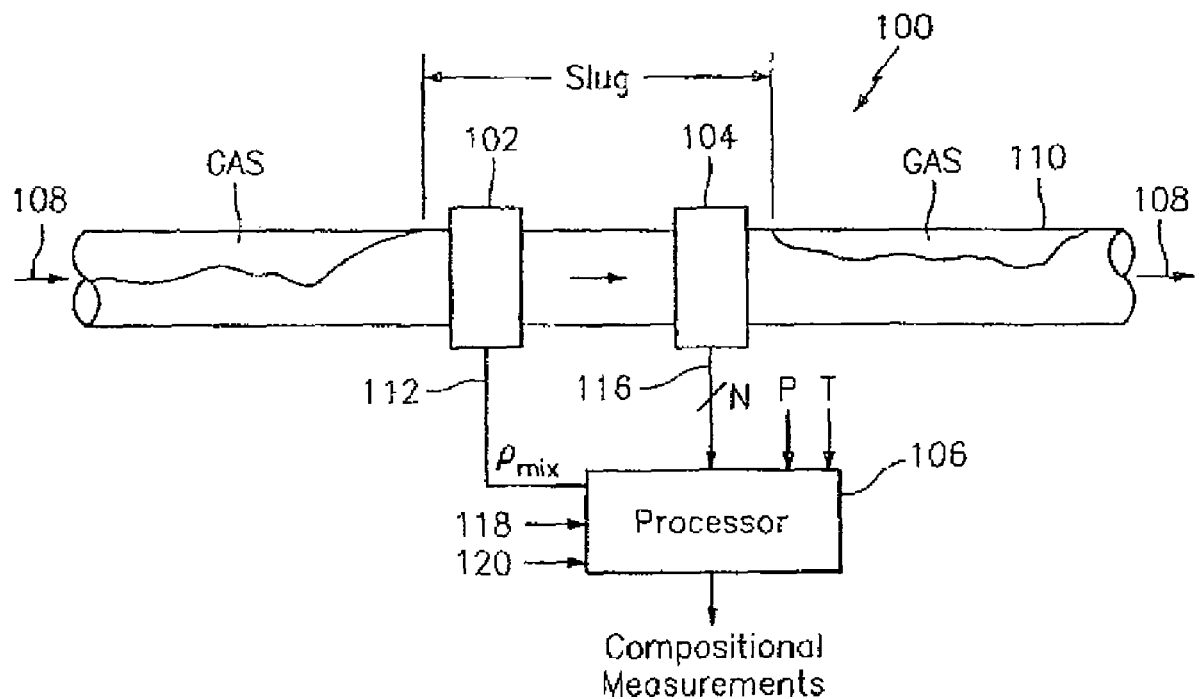
FIG. 2 is a schematic illustration of a flow measuring system for providing a density, composition, velocity and/or volumetric flow rate of the mixture wherein the mixture is shown having a temporal variation in the gas void fraction in accordance with the present invention.

However, the system 100 may work intermittently for mixtures 108 that do not fill the pipe 110 and/or that have a gas void fraction over the predetermined level. Such an inconsistent flow having temporal variations in the levels of the gas void fractions can be found in pipes at well heads, wherein in these instances, the oil, water and gas mixtures 108 flowing from the well (as shown in FIG. 2) through a pipe 110 tend to have random temporal variations of gas void fraction. In these flows, it has also been noticed that periodically slugs of fluid (i.e., bodies of liquid consisting of one or both of oil and water, which bodies occupy a substantial amount of the cross-sectional area of the pipe at a given location) flow through the pipe 110 for varying periods of time where the pipe 110 is near full or full and has a correspondingly low or nil gas void fraction. During this slugging period or window, the conditions are satisfactory for measuring the gas void fraction using the sonar meter 104, provided the period of the slug is at least 6-10 seconds in duration or sufficient time has elapsed for the sonar meter 104 to determine a gas void fraction measurement.

Figure 3A:
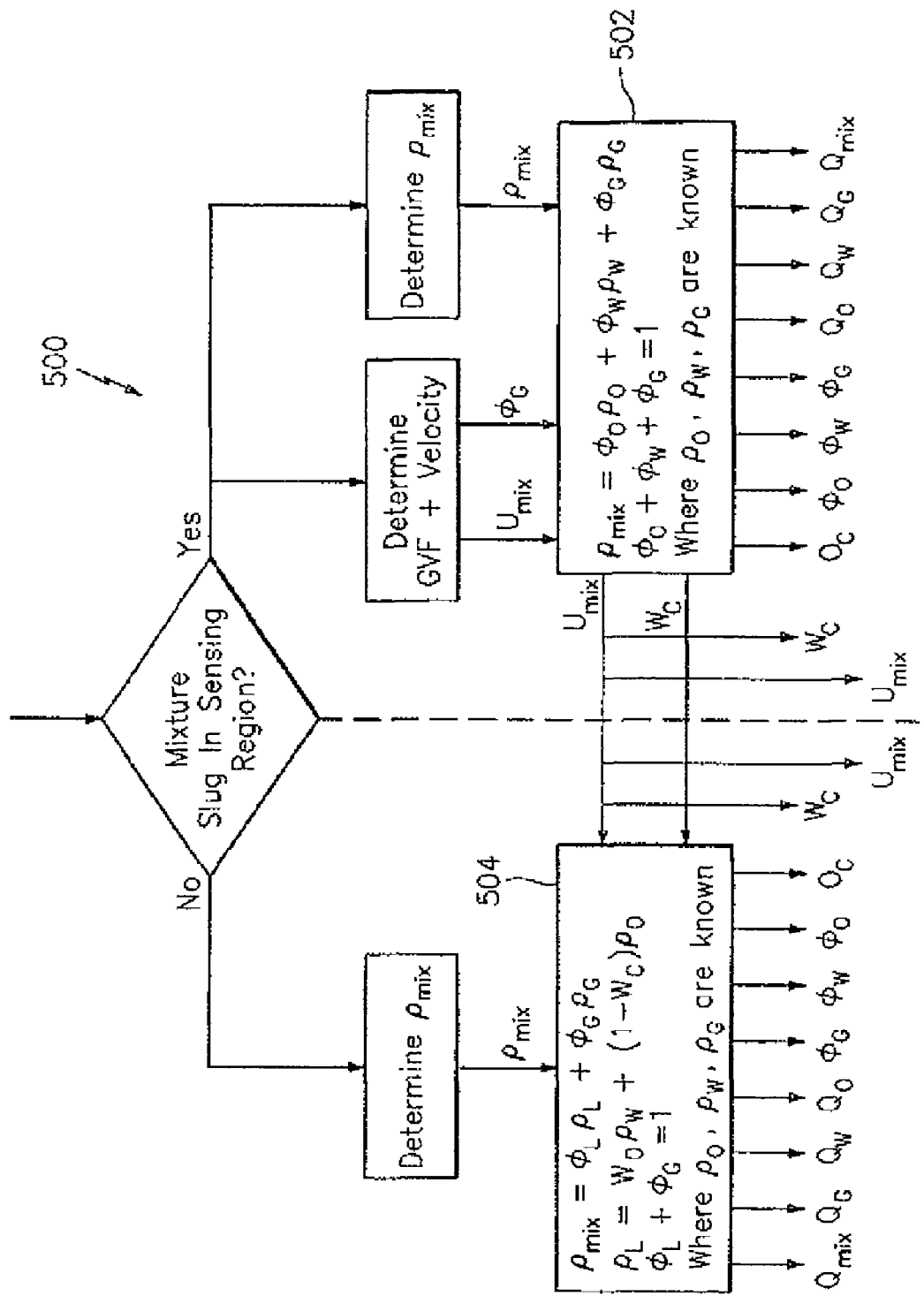
FIG. 3a is a block diagram of the processor of the transmitter of the system of FIG. 1 and FIG. 2 to provide a continuous real-time measurement of the mixture in accordance with the present invention.

Referring to FIG. 3a, a block diagram 500 illustrating one embodiment of a method for providing a continuous real-time measurement of the mixture 108, in accordance with the present invention is shown. If a slug is in the sensing regions of the meters 102 and 104 for a sufficient time period, the sonar meter 104 is able to measure the gas void fraction ($\phi_G$) and the flow velocity ($U_{mix}$) of the mixture 108 and the density meter 102 is able to measure the density of the mixture ($\rho_{mix}$) 108. At this point, the density of the oil ($\rho_O$), the density of the water ($\rho_W$), the density of the gas ($\rho_G$), the density of the mixture 108 ($\rho_{mix}$) and the phase fraction of the gas ($\phi_G$) are known. However, the phase fraction of the oil ($\rho_O$) and the phase fraction of the water ($\phi_W$) are still unknown. It is assumed that the water cut will not significantly change between the slugging period and the non-slugging period. As shown in operational block 502 in FIG. 3a, these two unknowns ($\phi_o$, $\phi_w$) may be solved to determine the desired parameters using the relationships given by, $$\rho_{mix} = \phi_O \rho_O + \phi_W \rho_W + \phi_G \rho_G, \quad \text{Eqn. (1)}$$

and $$\phi_O + \phi_W + \phi_G = 1. \quad \text{Eqn. (2)}$$

where $\rho_{mix}$ is the density of the mixture, $\rho_O$ is the density of the oil, $\rho_W$ is the density of the water, $\rho_G$ is the density of the gas, $\phi_O$ is the phase fraction of the oil, $\phi_W$ is the phase fraction of the water and $\phi_G$ is the phase fraction of the gas. Additionally, the velocity measured by the sonar meter 104 can be used.

Thus, knowing the velocity of the mixture 108, the cross-section area of the pipe 110, and the phase fractions $\phi_o$, $\phi_w$, $\phi_G$, the volumetric flow rates $Q_0$, $Q_w$, $Q_o$, $Q_{mix}$ of the mixture 108, the oil cut $O_c$, and the water cut $W_c$ may be also determined. As such, it should be appreciated that the water cut $W_C$ may be expressed via the relationship given by, $$W_c = \frac{Q_W}{Q_O + Q_W}, \quad \text{Eqn. (3)}$$

$$\phi_w = \frac{A_W}{A_{pipe}}, \quad \text{Eqn. (4)}$$

and $$Q_W = A_{pipe} \varphi_W U_{mix}, \quad \text{Eqn. (5)}$$

where $Q_W$ is the volumetric flow rate of the water phase and $Q_O$ is the volumetric flow rate of the oil phase, $A_W$ is the cross sectional area of the water component, $A_{pipe}$ is the cross sectional area of the pipe 110 and $U_{mix}$ is the volumetric flow rate of the mixture. While the equations to determine the water cut ($W_c$) and the volumetric flow of the water ($Q_w$) are shown, similar equations to determine the volumetric flow of the other phase and oil cut may be determined.

Alternatively, when the sensing region does not have a slug, the gas void fraction can not be measured by the sonar meter 104, however the density meter 102 can still measure the density of the mixture. For this period of time, the system 100 can still measure the parameters shown in FIG. 3a to provide a real time continuous measurement of the mixture 108. During this period, the density meter 102 measures the density of the mixture 108 ($\rho_{mix}$). As shown in operational block 504, the velocity of the mixture 108 ($U_{mix}$) and the water cut determined during the slug period/window is used to determine the parameters in a similar manner as that shown in operational block 502. At this point the density of the oil ($\rho_O$), the density of the water ($\rho_W$), the density of the gas ($\rho_G$), the density of the mixture 108 ($\rho_{mix}$) and the water cut (Wc) of the mixture 108 is known. However, the phase fraction of the liquid ($\phi_L$), the density of the liquid ($\rho_L$) and the phase fraction of the gas ($\phi_G$) are still unknown. As shown in operational block 504, these unknowns ($\phi_L$, $\rho_L$, $\phi_G$) may be solved to determine the desired parameters using the relationships given by, $$\rho_{mix} = \phi_L \rho_L + \phi_G \rho_G, \qquad \text{Eqn. (6)}$$

$$\rho_L = W_c \rho_W + (1 - W_C) \rho_O, \qquad \text{Eqn. (7)}$$

and $$\phi_L + \phi_G = 1. \qquad \text{Eqn. (8)}$$

where $\rho_{mix}$ is the density of the mixture, $\rho_O$ is the density of the oil, $\rho_W$ is the density of the water, $\rho_G$ is the density of the gas, $\rho_L$ is the phase fraction of the liquid, $\phi_L$ is the phase fraction of the liquid, $\phi_G$ is the phase fraction of the gas and Wc is the water cut of the mixture. Thus, the volumetric flow rates of the mixture 108 and each phase may now be determined.

It should be appreciated that identifying the relationship between the parameters allows for the determination of desired variables. For example, the density of any N-component mixture equals the sum of the individual component densities times the volumetric fraction and may be given by:

$$\rho = \sum_{i=1}^{N} \phi_i \rho_i, \qquad \text{Eqn. (9)}$$

with the constraint that $$\sum_{i=1}^{N} \phi_i = 1,$$

where $\rho$ is equal to the mixture density, $\phi_i$ is equal to the component volume fraction and $\rho_i$ is equal to the component density.

As such, for oil, water and gas mixtures the density as given by Eqn. (9) can be expressed as:

$$\rho = \phi_O \rho_O + \phi_W \rho_W + \phi_G \rho_G, \qquad \text{Eqn. (10)}$$

with the constraint that $\phi_O + \phi_W + \phi_G = 1$, where the O, W and G subscripts refer to oil, water and gas, respectively. Combining these equations, assuming $\phi_G \rho_G$ is small and solving for the volume fraction of the oil thus yields:

$$\phi_O = \frac{\rho - \rho_W(1 - \phi_G)}{\rho_O - \rho_W}, \qquad \text{Eqn. (11)}$$

Again starting with Eqn. (9), but this time assuming the mixture contains only oil and water, the oil fraction ($\phi'$) may be calculated as:

$$\phi'_O = \frac{\rho - \rho_W}{\rho_O - \rho_W}, \qquad \text{Eqn. (12)}$$

It should be appreciated that these equations differ only by the $1-\phi_G$ term. Referring to FIG. 3c, a graph illustrating the error in the oil volume fraction (and thus net oil rate) if this term is ignored when free gas is present is shown. It should be appreciated that the errors in the net oil measurement are significant and will result in a gross overstatement of the net oil rate. For example with only a 1% gas void fraction, the error in the oil fraction is between 30 and >100% depending on the oil gravity. Whereas if the free gas is accurately measured and accounted for when calculating the oil fraction, the error is eliminated. The remaining sections describe a sonar-based method of measuring the free gas and present some experimental and field data demonstrating the measurement concept.

Figure 3B:
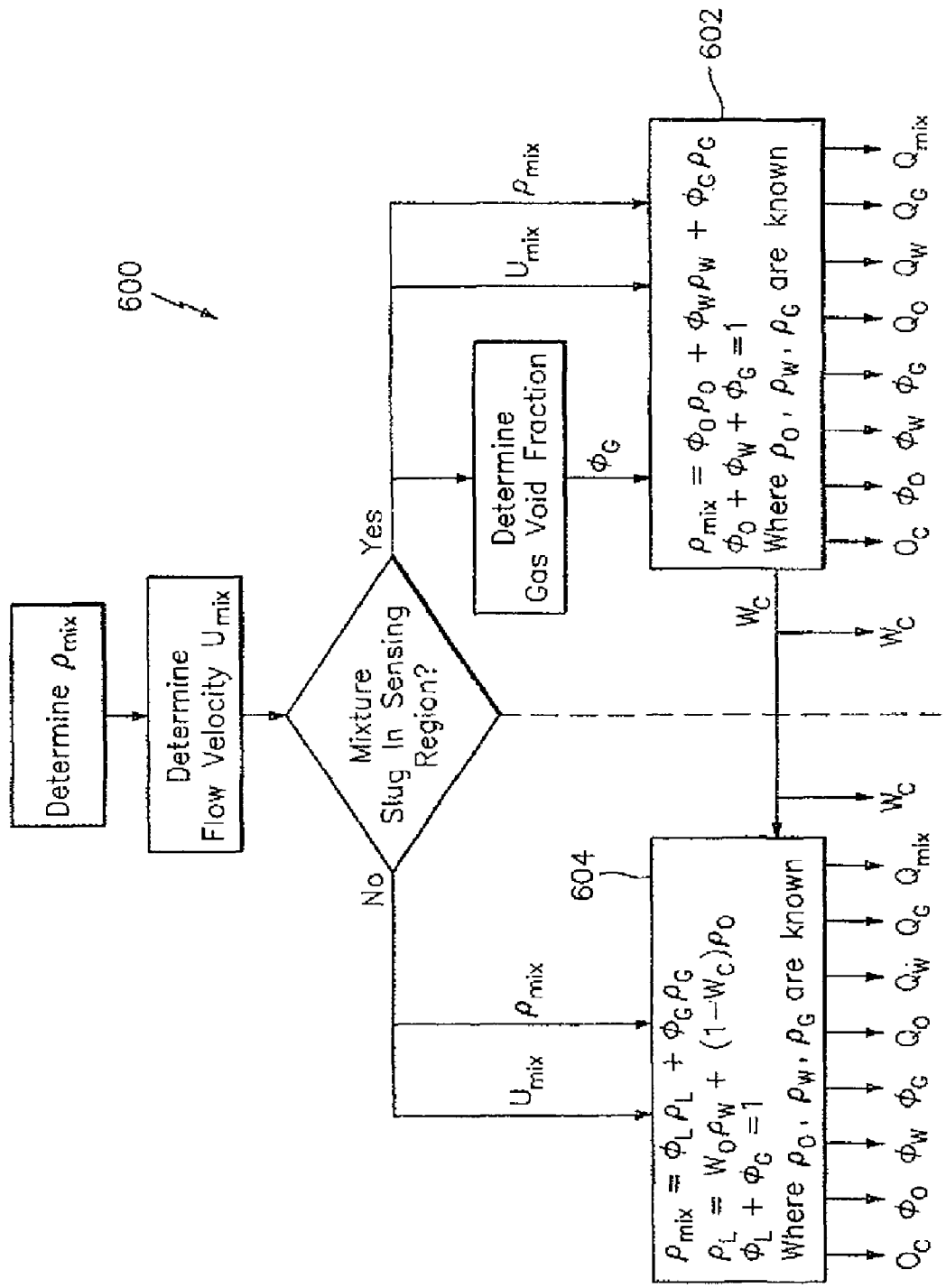
FIG. 3b is another embodiment of a block diagram of the processor of the transmitter of the system of FIG. 1 and FIG. 2 to provide a continuous real-time measurement of the mixture in accordance with the present invention.
Figure 3C:
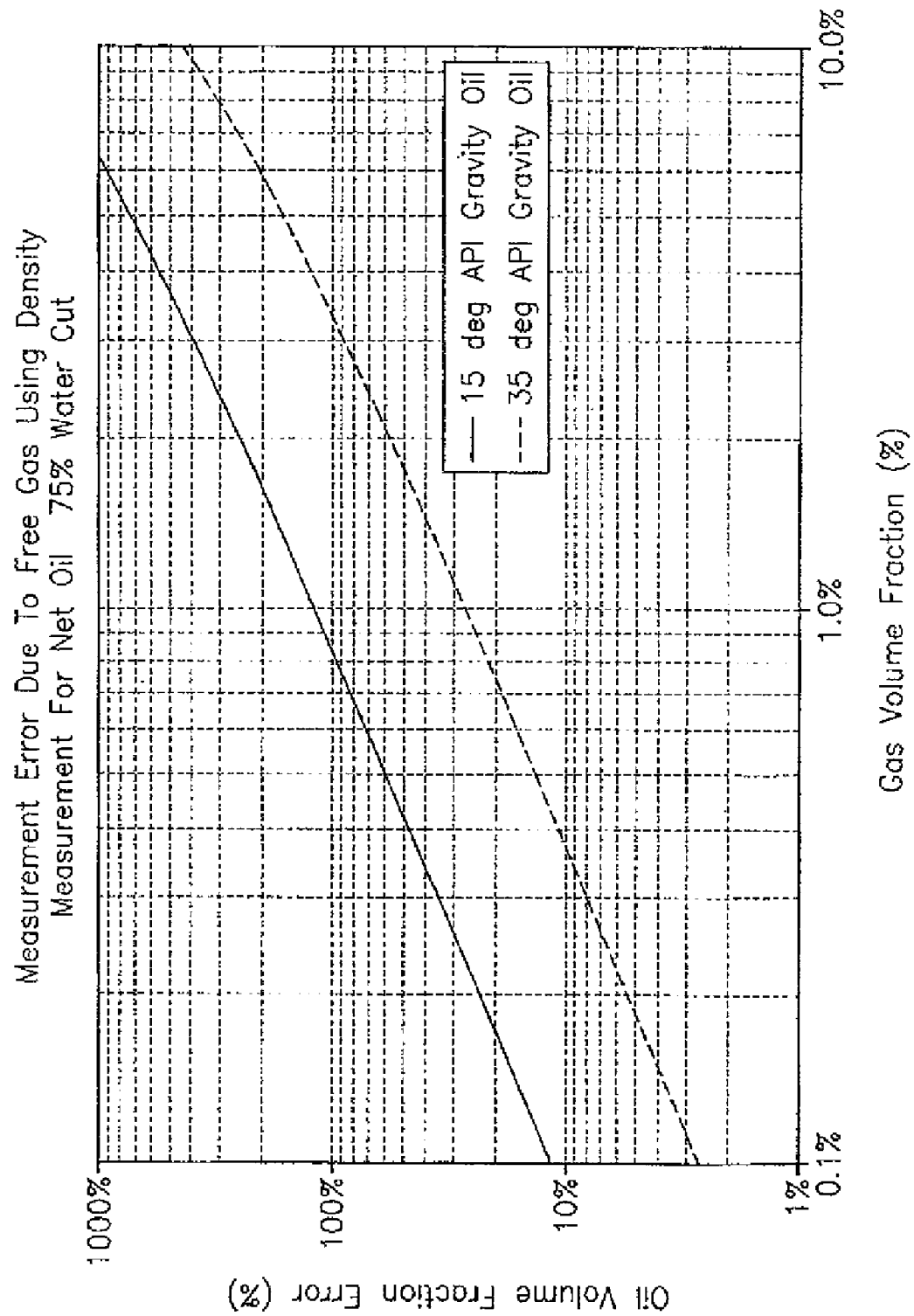
FIG. 3c is a illustrating the error in the oil volume fraction when free gas is present and when the $1-\phi_G$ term is ignored.

Referring to FIG. 3b, a block diagram 600 illustrating an alternative embodiment of a method for providing a continuous real-time measurement of the mixture 108, in accordance with the present invention is shown. It should be appreciated that the processing unit 106 may process the data provided by the density meter 102 and the sensor array 124-130 to provide the same measurements as described hereinbefore. As shown, the density of the mixture 108 is continually measured by the density meter 102 and the velocity of the mixture 108 is continually measured using the sensor arrays 124-130. When a slug is passing through the sensing region, as described hereinbefore, the sensor array 124-130 measures the gas void fraction (GVF) ($\phi_G$) of the mixture 108, wherein the density ($\rho_{mix}$) of the mixture 108 and the flow velocity ($U_{mix}$) of the mixture 108 is determined beforehand by any method and/or device suitable to the desired end purpose. It should be appreciated that at this point, the density of the oil ($\rho_O$), the density of the water ($\rho_W$), the density of the gas ($\rho_G$), the density of the mixture 108 ($\rho_{mix}$), the phase fraction of the gas ($\rho_G$) and the flow velocity ($U_{mix}$) of the mixture 108 is known. However, the phase fraction of the oil ($\phi_O$) and the phase fraction of the water ($\phi_W$) are still unknown. Now having the two unknown parameters ($\phi_G$, $\phi_W$) and given the relationships as described in Eqn. 1 and Eqn. 2 as shown in operational block 602, the water phase fraction ($\phi_W$) (or water cut) and the oil phase fraction ($\phi_O$) (or oil cut) can be determined as described in greater detail hereinbefore. Also, as described in greater detail hereinbefore, a number of other parameters of the mixture 108 also may be determined.

In a similar fashion to that described hereinbefore, when a slug is not within the sensing region (as may be defined by the foot print of the sensor array 124-130), the measured density, the measured flow velocity, and the measured GVF (measured during the slugging period) may be used to determine the parameters of the mixture 108, as shown in operational block 604 and similar to operational block 504 as described hereinbefore.

Figure 4:
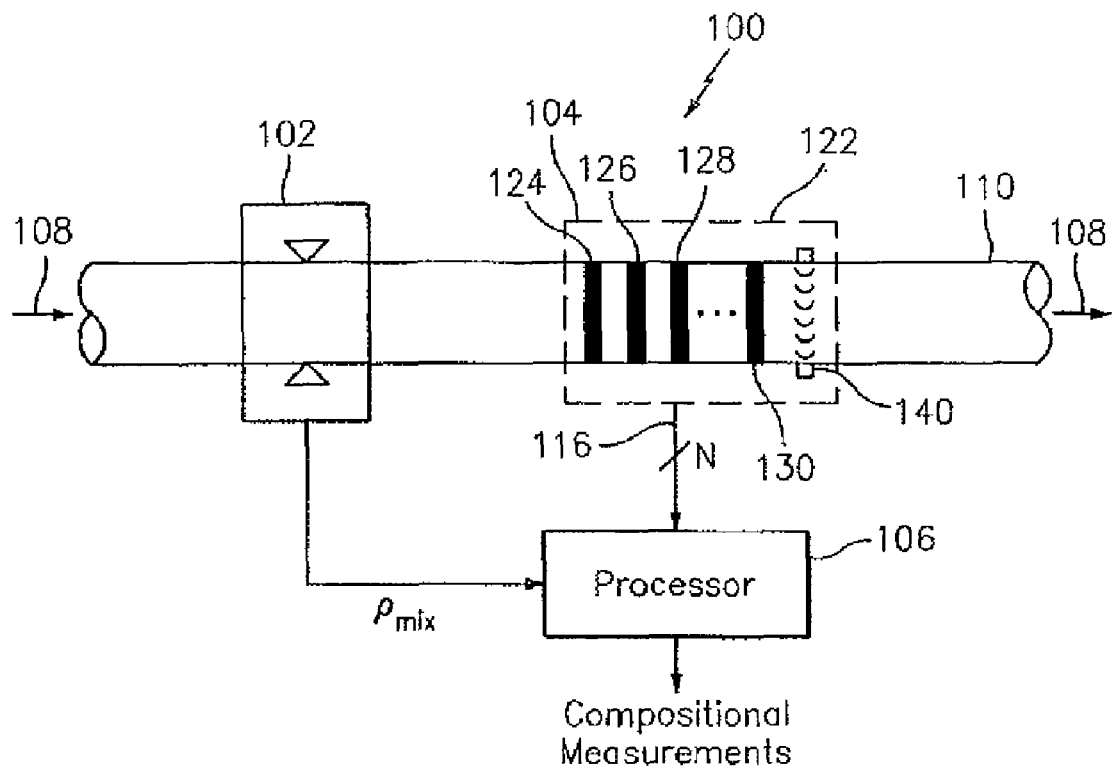
FIG. 4 is a schematic illustration of another embodiment of a flow measuring system for providing a density, composition, velocity and/or volumetric flow rate of the mixture in accordance with the present invention.

FIG. 4 illustrates another embodiment of the present invention, wherein the sensor array 124-130 includes an ultrasonic sensor 140 that includes a transmitter and receiver for transmitting and receiving an ultrasonic signal propagating through the mixture 108. The processing unit 106 is operable to determine the time of flight of the ultrasonic signal within the mixture between the transmitter and receiver, and the time of flight can be used to determine if a liquid slug is present within the cross-sectional area of the pipe aligned with the sensor 140. In some embodiments, the time of flight value is used to calculate the speed of sound within the mixture 108. If the speed of sound is within a certain range of values that correlates to liquids (which values are significantly different in magnitude than the same for gases), then it can be determined that a slug is present at the location of the sensor 140.

Figure 5:
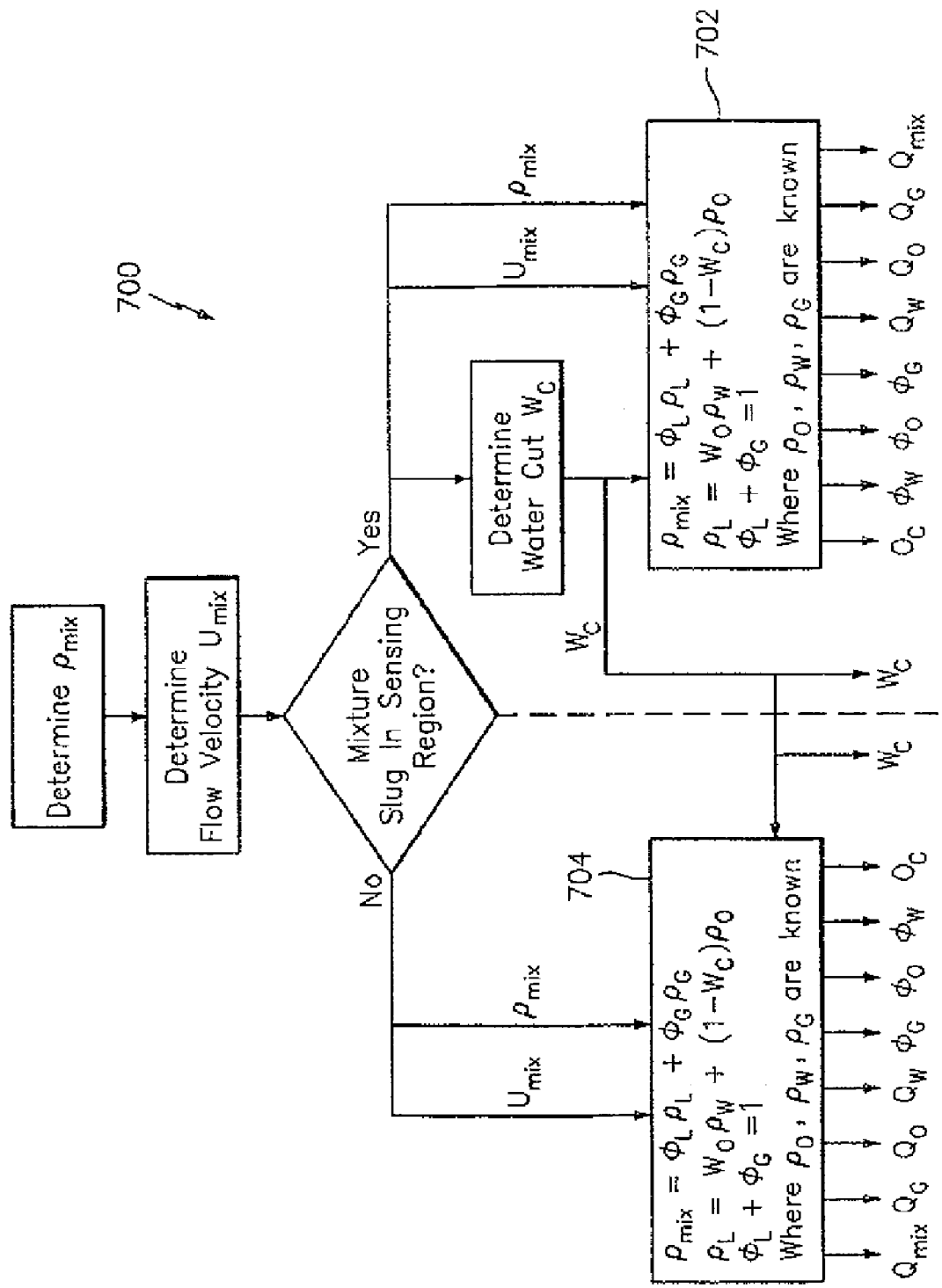
FIG. 5 is a block diagram of the processor of the transmitter of the system of FIG. 4 to provide a continuous real-time measurement of the mixture in accordance with the present invention.

It should also be appreciated that the density meter 102 may continuously measure the density of the mixture ($\rho_{mix}$), the sensor array 124-130 may continually measure the velocity of the mixture ($U_{mix}$), and during the slugging period, the ultrasonic sensor 140 may measure the speed of sound propagating through the liquid. Referring to FIG. 5, a block diagram 700 illustrating still yet another alternative embodiment of a method for providing a continuous real-time measurement of the mixture 108, in accordance with the present invention is shown. Knowing the speed of sound of the liquid using the ultrasonic sensor, the water cut may be determined, similar to that described herein and in U.S. patent application Ser. No. 11/442,954 filed on May 30, 2006 and U.S. Pat. No. 7,096,719, which are incorporated herein by reference in their entirety. As shown in FIG. 5, the speed of sound of the liquid is measured when a slug is present in the sensing region (i.e., within the cross-section of the pipe, sometimes referred to as the "foot print" of the ultrasonic sensor, aligned with the ultrasonic sensor). It should be appreciated that the time required to measurement of the speed of sound to determine the water cut using the ultrasonic sensor 140 allows for a faster measurement than that normally provided by a sensor array 124-130 not having an ultrasonic sensor 140, and thus a small slug (i.e., one that takes a substantially shorter period of time to pass the sensor 140 than is required) is sufficient to provide a water cut measurement, wherein the processing is similar to that described hereinbefore.

If a slug is in the sensing regions of the meters 102 and 104 for a sufficient time period, the water cut ($W_c$) is measured. The water cut (Wc) may then be used with the density ($\rho_{mix}$) of the mixture 108 and the flow velocity ($U_{mix}$) of the mixture 108, which are determined beforehand by any method and/or device suitable to the desired end purpose, to determine the desired parameters. At this point, although the density of the water ($\rho_W$), the density of the gas ($\rho_G$), the density of the mixture 108 ($\rho_{mix}$), the flow velocity ($U_{mix}$) of the mixture 108, the density of the oil ($\rho_O$) and the water cut is known, the phase fraction of the liquid ($\phi_L$) the density of the liquid ($\rho_L$) and the phase fraction of the gas ($\phi_G$) are still unknown. As shown in operational block 702 in FIG. 5, these three unknowns ($\phi_L, \phi_G, \rho_L$) may be solved to determine the desired parameters using the relationships given by, $$\rho_{mix} = \phi_L \rho_L + \phi_G \rho_G, \quad \text{Eqn. (13)}$$

$$\rho_L = W_C \rho_W + (1 - W_C) \rho_O, \quad \text{Eqn. (14)}$$

and $$\phi_L + \phi_G = 1. \quad \text{Eqn. (15)}$$

where $\rho_{mix}$ is the density of the mixture, $\rho_G$ is the density of the gas, $\rho_L$ is the density of the liquid, $\phi_L$ is the phase fraction of the liquid, Wc is the water cut, $\rho_O$ is the phase fraction of the oil and $\phi_G$ is the phase fraction of the gas. This allows for the determination of the water cut (Wc), the oil cut (Oc), the phase fraction of the water ($\phi_W$), the phase fraction of the oil ($\phi_O$), the phase fraction of the gas ($\phi_G$), the volumetric flow rate of the water ($Q_W$), the volumetric flow rate of the oil ($Q_O$), the volumetric flow rate of the gas ($Q_G$) and the volumetric flow rate of the mixture ($Q_{mix}$), as described hereinbefore. Alternatively as shown in operational block 704, when the pipe 110 is not full (or slugging), the parameters may still be determined using the measured density ($\rho_{mix}$) of the mixture 108, the measured velocity ($U_{mix}$) of the mixture 108 and the water cut (Wc) measured during the slugging period, as similarly described hereinbefore.

Figure 6:
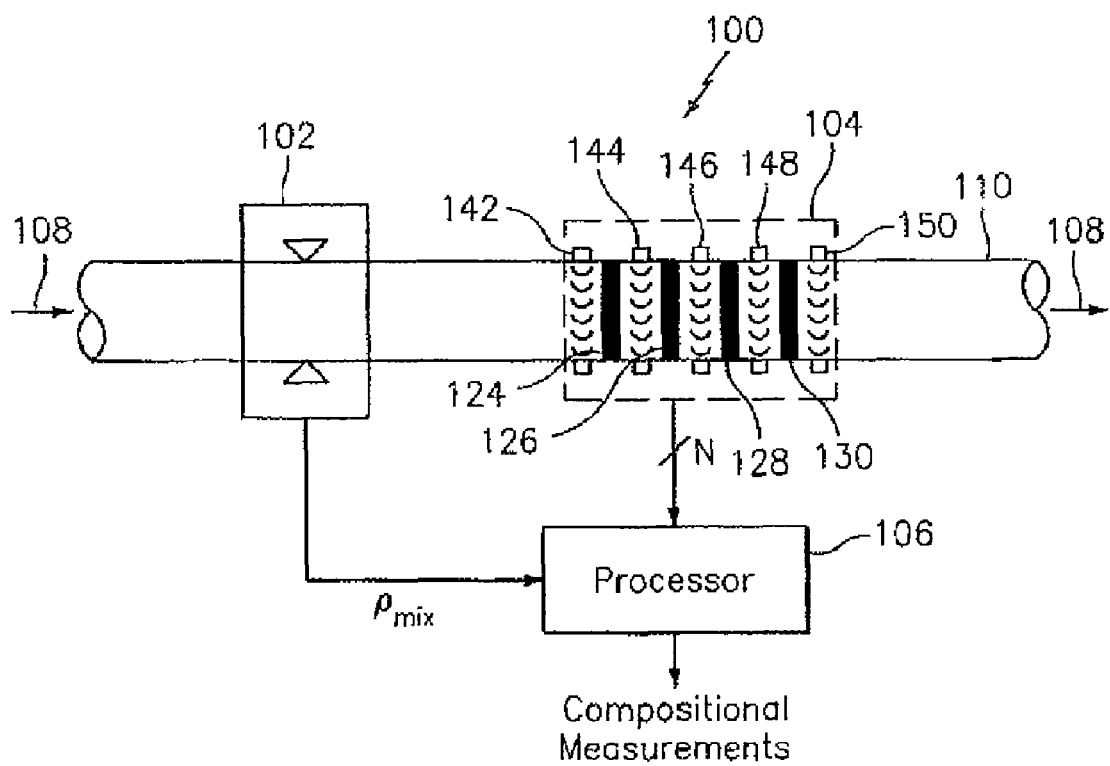
FIG. 6 is a schematic illustration of another embodiment of a flow measuring system for providing a density, composition, velocity and/or volumetric flow rate of the mixture in accordance with the present invention.

FIG. 6 illustrates another embodiment of the present invention and includes both an array of strain sensors 124-130 and an array of ultrasonic sensors 142-148. As shown, the array of strain sensors 124-130 and array of ultrasonic sensors 142-148 are interlaced such that a strain sensor and ultrasonic sensor are alternately disposed axially along the pipe 110. While shown interlaced, one skilled in the art will appreciate that the strain sensor array 124-130 and the ultrasonic sensor array 142-148 may be disposed axially adjacent to each other, and not interlaced, similar to that shown in U.S. Pat. No. 7,237,440, which is incorporated herein by reference in its entirety. The array of ultrasonic sensors 142-148 provide a second means for measuring the velocity of the fluid mixture ($U_{mix}$). In addition, an extra ultrasonic sensor (e.g., 150) may be independently used to determine the speed of sound propagating through the liquid (and hence the water cut) or one of the ultrasonic sensors used to measure velocity may also be used to measure the speed of sound propagating through the liquid.

Figure 7:
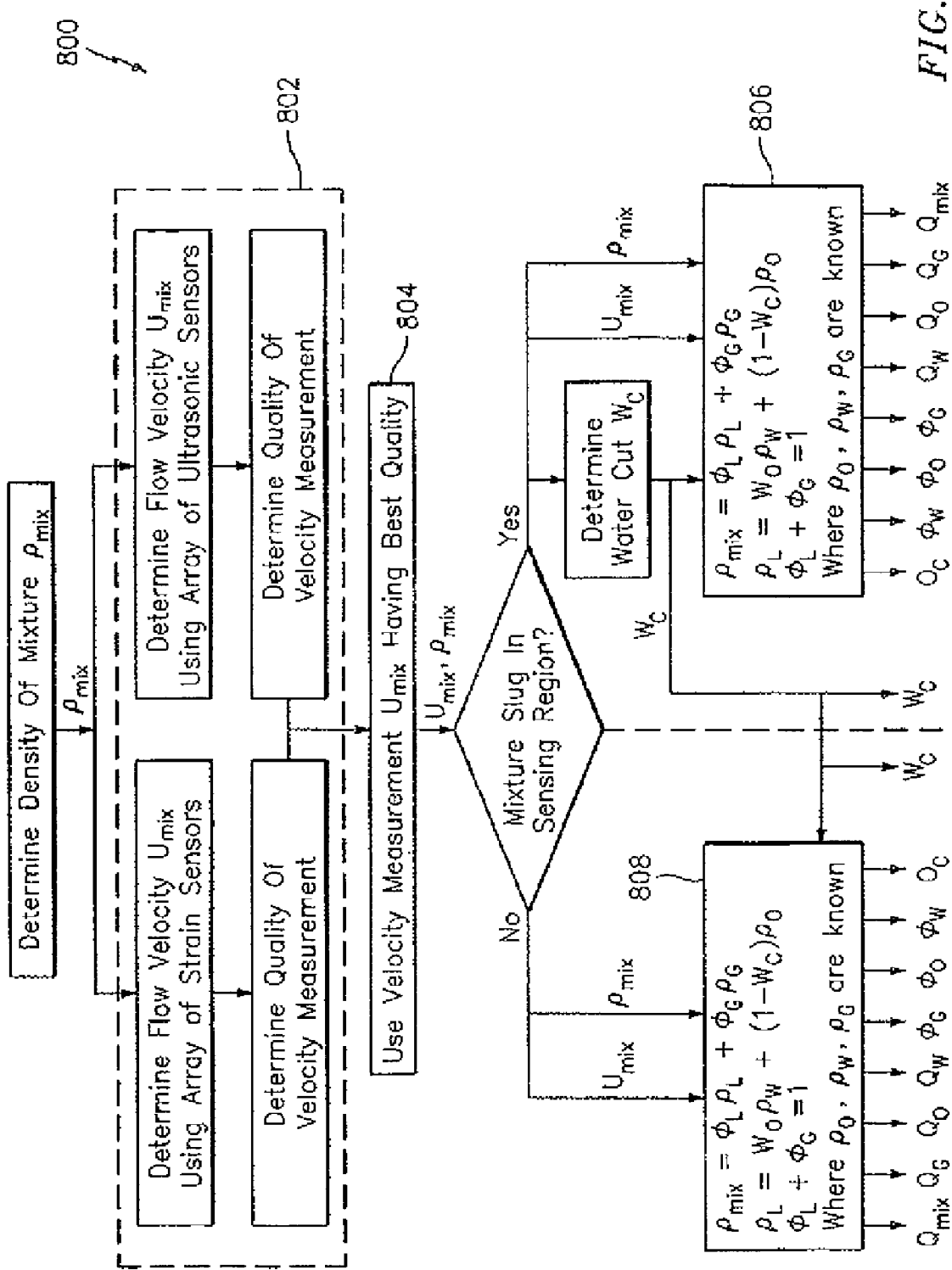
FIG. 7 is a block diagram of the processor of the transmitter of the system of FIG. 6 to provide a continuous real-time measurement of the mixture in accordance with the present invention.

As shown in FIG. 7, it should be further appreciated that although the processing unit 106 may process the data from the strain sensors and ultrasonic sensors in a similar method as that shown in FIG. 4 and FIG. 5, the array of ultrasonic sensors 142-148 may also provide a second means of measuring the velocity of the mixture 108. Referring to FIG. 7, a block diagram 800 illustrating still yet another alternative embodiment of a method for providing a continuous real-time measurement of the mixture 108, in accordance with the present invention is shown. As shown, both sensor arrays provide continuous output of the velocity of the mixture 108 in the pipe 110. The processing unit 106 continually evaluates the quality of each of the velocity measurements, as shown in operational block series 802 and similar to that described in U.S. Pat. No. 7,153,003, which is incorporated herein by reference in its entirety.

Figure 8A:
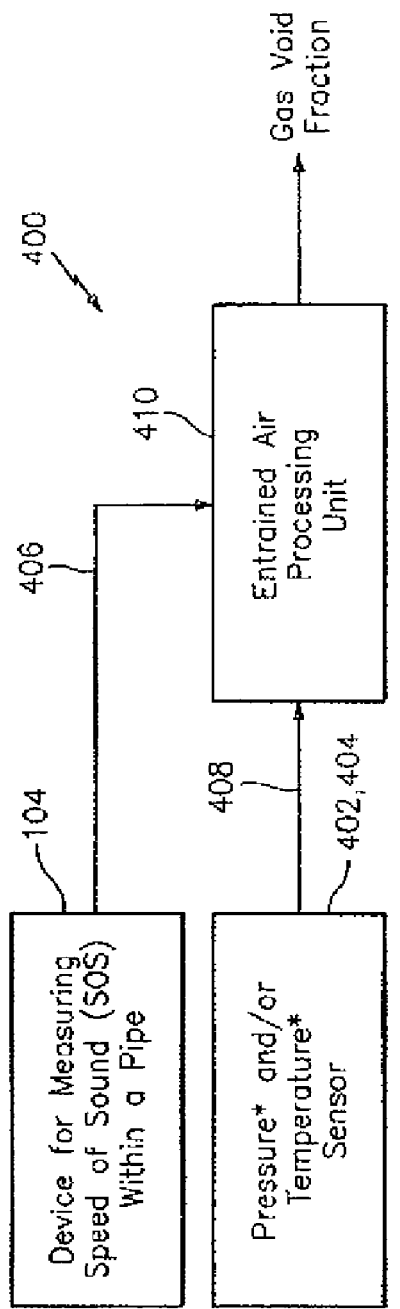
FIG. 8a is a block diagram illustrating one embodiment for measuring the volumetric flow and gas volume fraction of the mixture flowing in the pipe having entrained gas/air therein, in accordance with the present invention.

FIG. 8a is a block diagram 400 of one embodiment of the apparatus 100 of the present invention and includes a sonar meter 104 for measuring the speed of sound (SOS) propagating through the flow 108 within a pipe 110. A pressure sensor and/or temperature sensor 402, 404 may measure the pressure and/or temperature, respective, of the mixture 108 flowing through the pipe 110. In response to the speed of sound signal 406 and the characteristics 408 of the flow 108 (e.g., pressure and temperature), an entrained gas processing unit 410 determines the gas void fraction (GVF) of the flow 108. The pressure and temperature sensors 402, 404 enable the apparatus 100 to compensate or determine the gas volume fraction for dynamic changes in the pressure and temperature of the flow 108. Alternatively, the pressure and/or temperature may be estimated rather than actually measured.

Figure 8B:
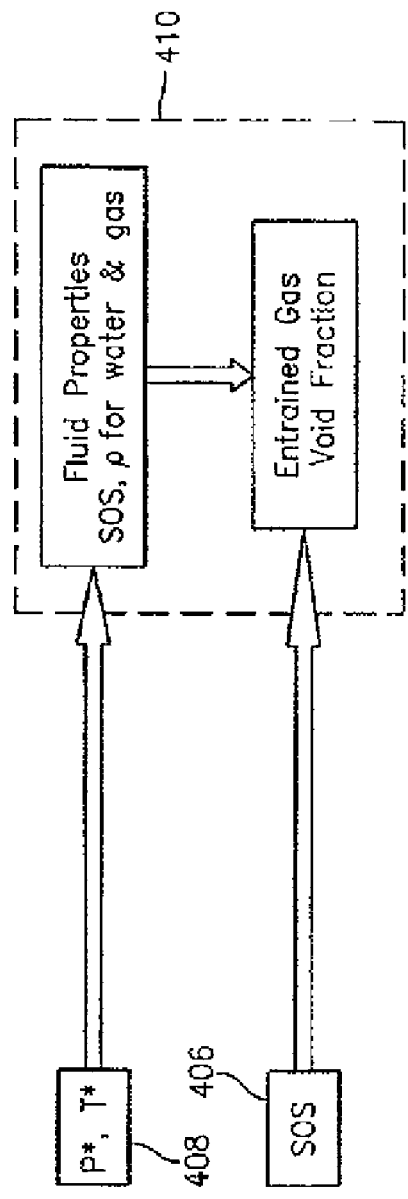
FIG. 8b is a functional flow diagram of an apparatus embodying the present invention that compensates the volumetric flow measurement of a volumetric flow meter, in accordance with the present invention.

A flow chart 412 shown in FIG. 8b illustrates the function of the entrained gas processing unit 410. As shown in FIG. 5a, the inputs to the processing unit 410 include the speed of sound (SOS) 406 within the mixture 108 in the pipe 110, and the pressure and/or temperature of the mixture 108. The fluid properties of the mixture 108 (e.g., SOS and density) are determined knowing the pressure and temperature of the mixture 108. The gas void fraction of the mixture 108 (GVF) is determined using the SOS measurement and fluid properties, which are described in greater detail herein.

Other information relating to the gas void fraction in a fluid and the speed of sound (or sonic velocity) in the fluid, is described in "Fluid Mechanics and Measurements in two-phase flow Systems", Institution of mechanical engineers, proceedings 1969-1970 Vol. 184 part 3C, Sep. 24-25, 1969, Birdcage Walk, Westminster, London S. W. 1, England, which is incorporated herein by reference in its entirety.

Figure 9:
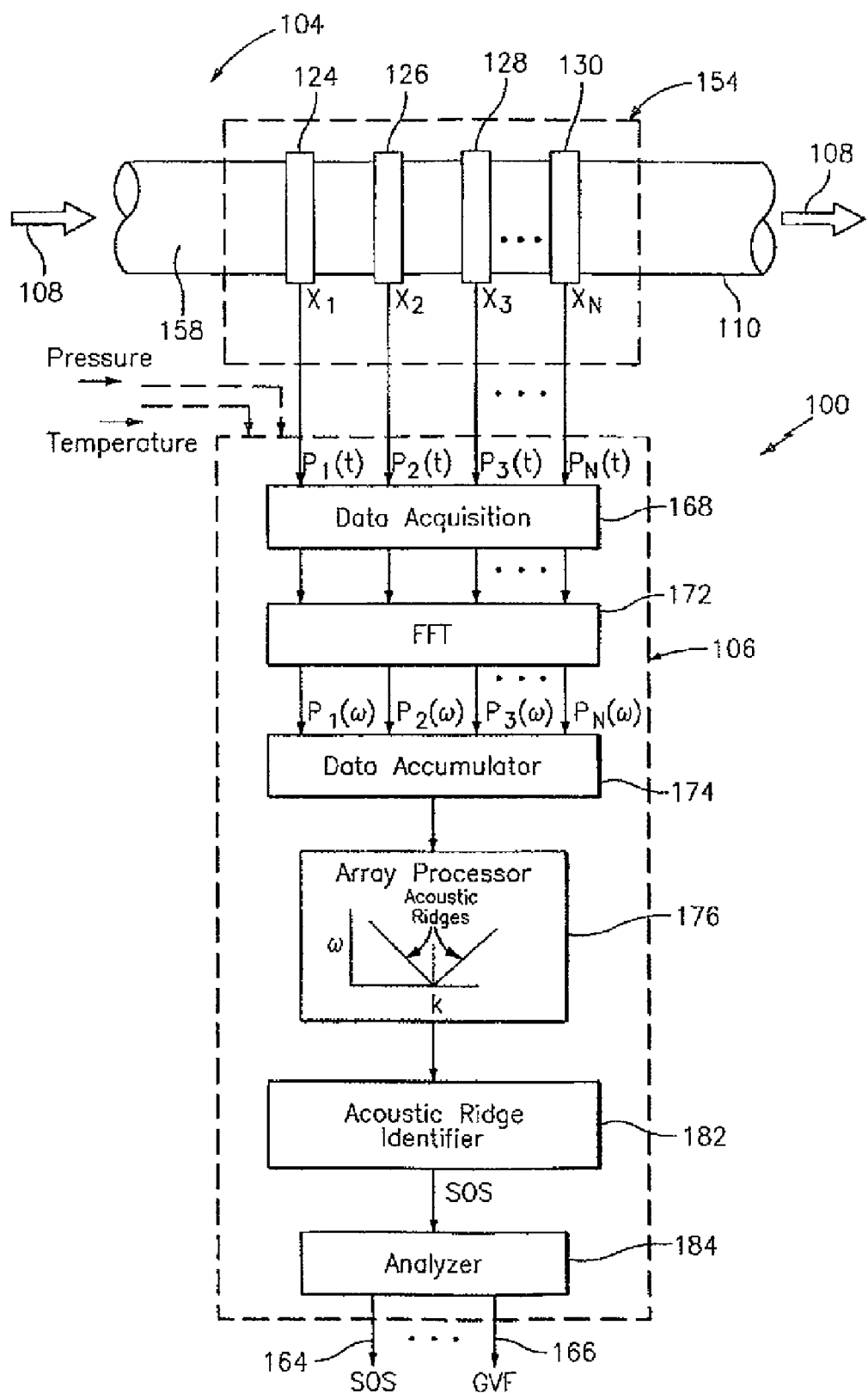
FIG. 9 is a schematic block diagram of a gas void fraction meter, in accordance with the present invention.

FIG. 9 illustrates the sonar meter 104 of FIG. 2, as described hereinbefore. The sonar meter 104 includes a sensing device 154 disposed on the pipe 110 and a processing unit 106. The sensing device 154 comprises an array of strain-based sensors or pressure sensors 124-130 for measuring the unsteady pressures produced by acoustic waves propagating through the flow 108 to determine the speed of sound (SOS). The pressure signals $P_1(t)$-$P_N(t)$ are provided to the processing unit 106, which digitizes the pressure signals and computes the SOS and GVF parameters. A cable electronically connects the sensing device 154 to the processing unit 106. The analog pressure sensor signals $P_1(t)$-$P_N(t)$ are typically 4-20 mA current loop signals.

The array of pressure sensors 124-130 comprises an array of at least two pressure sensors 124,126 spaced axially along the outer surface 158 of the pipe 110, having a process flow 108 propagating therein. The pressure sensors 124-130 may be clamped onto or generally removably mounted to the pipe 110 by any releasable fastener, such as bolts, screws and clamps. Alternatively, the sensors may be permanently attached to, ported in or integral (e.g., embedded) with the pipe 110. The array of sensors of the sensing device 154 may include any number of pressure sensors 124-130 greater than two sensors, such as three, four, eight, sixteen or N number of sensors between two and twenty-four sensors. Generally, the accuracy of the measurement improves as the number of sensors in the array increases. The degree of accuracy provided by the greater number of sensors is offset by the increase in complexity and time for computing the desired output parameter of the flow. Therefore, the number of sensors used is dependent at least on the degree of accuracy desired and the desire update rate of the output parameter provided by the apparatus 100. The pressure sensors 124-130 measure the unsteady pressures produced by acoustic waves propagating through the flow 108, which are indicative of the SOS propagating through the fluid flow 108 in the pipe 110. The output signals $(P_1(t)$-$P_N(t))$ of the pressure sensors 124-130 are provided to a pre-amplifier unit that amplifies the signals generated by the pressure sensors 124-130. The processing unit 106 processes the pressure measurement data $P_1(t)$-$P_N(t)$ and determines the desired parameters and characteristics of the flow 108, as described hereinbefore. Although the sensing device 154 is shown as being comprised of an array of pressure sensors 124-130, it should be appreciated that the sensing device 154 may also include ultrasonic sensors, individual or in an array fashion and/or a combination of ultrasonic sensors and pressure sensors, in both individual and array fashion.

The apparatus 100 also contemplates providing one or more acoustic sources to enable the measurement of the speed of sound propagating through the flow 108 for instances of acoustically quiet flow. The acoustic source may be a device that taps or vibrates on the wall of the pipe 110, for example. The acoustic sources may be disposed at the input end of output end of the array of sensors 124-130, or at both ends as shown. One should appreciate that in most instances the acoustics sources are not necessary and the apparatus passively detects the acoustic ridge provided in the flow 108, as will be described in greater detail hereinafter. The passive noise includes noise generated by pumps, valves, motors, and the turbulent mixture itself.

As suggested and further described in greater detail hereinafter, the apparatus 100 has the ability to measure the speed of sound (SOS) by measuring unsteady pressures created by acoustical disturbances propagating through the flow 108. Knowing or estimating the pressure and/or temperature of the flow and the speed of sound of the acoustic disturbances or waves, the processing unit 106 can determine gas void fraction, such as that described in U.S. Patent Application Publication No. 20030154036, U.S. Pat. Nos. 7,032,432 and 7,062,976, which are all incorporated by reference in their entireties.

The sonar meter 104 of FIG. 1 embodying the present invention has an array of at least two pressure sensors 124, 126, located at two locations $x_1, x_2$ axially along the pipe 110 for sensing respective stochastic signals propagating between the sensors 124,126 within the pipe at their respective locations. Each sensor 124,126 provides a signal indicating an unsteady pressure at the location of each sensor, at each instant in a series of sampling instants. One will appreciate that the sensor array 124-130 may include more than two pressure sensors as depicted by pressure sensor 124,126 at location $x_3, x_N$. The pressure generated by the acoustic pressure disturbances may be measured through strained-based sensors and/or pressure sensors 124-130. The pressure sensors 124-130 provide analog pressure time-varying signals $P_1(t)$, $P_2(t)$, $P_3(t)$, $P_N(t)$ to the signal processing unit 106. The processing unit 106 processes the pressure signals to first provide output signals 164, 166 indicative of the speed of sound propagating through the flow 108, and subsequently, provide a GVF measurement in response to pressure disturbances generated by acoustic waves propagating through the flow 108.

The processing unit 106 receives the pressure signals from the array of sensors 124-130. A data acquisition unit 168 digitizes pressure signals $P_1(t)$-$P_N(t)$ associated with the acoustic waves propagating through the pipe 110. An FFT logic 172 calculates the Fourier transform of the digitized time-based input signals $P_1(t)$-$P_N(t)$ and provide complex frequency domain (or frequency based) signals $P_1(\omega)$, $P_2(\omega)$, $P_3(\omega)$, $P_N(\omega)$ indicative of the frequency content of the input signals.

A data accumulator 174 accumulates the additional signals $P_1(t)$-$P_N(t)$ from the sensors, and provides the data accumulated over a sampling interval to an array processor 176, which performs a spatial-temporal (two-dimensional) transform of the sensor data, from the x-t domain to the k-ω domain, and then calculates the power in the k-ω plane, as represented by a k-ω plot, similar to that provided by the convective array processor 194 as discussed in further detail hereinafter.

To calculate the power in the k-ω plane, as represented by a k-ω plot (see FIG. 10) of either the signals or the differenced signals, the array processor 176 determines the wavelength and so the (spatial) wavenumber k, and also the (temporal) frequency and so the angular frequency ω, of various of the spectral components of the stochastic parameter. It should be appreciated that there are numerous algorithms available in the public domain to perform the spatial/temporal decomposition of arrays of sensor units 124-130 and any of those may be used suitable to the desired end purpose.

Figure 10:
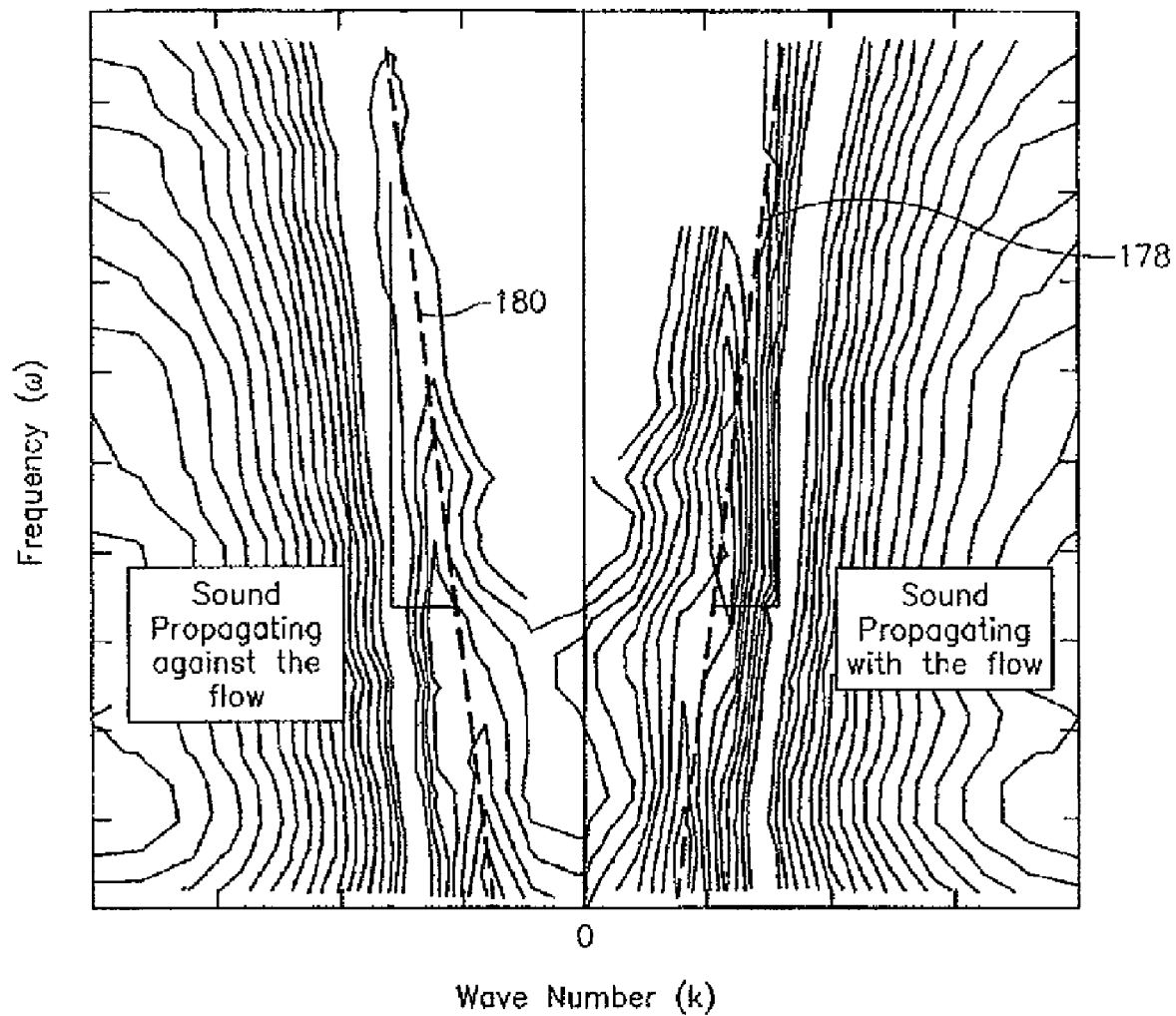
FIG. 10 is a schematic block diagram of another embodiment of gas void fraction meter, in accordance with the present invention.

In the case of suitable acoustic waves being present in both axial directions, the power in the k-ω plane shown in a k-ω plot of FIG. 10 so determined will exhibit a structure that is called an acoustic ridge 178,180 in both the left and right planes of the plot, wherein one of the acoustic ridges 178 is indicative of the speed of sound traveling in one axial direction and the other acoustic ridge 180 being indicative of the speed of sound traveling in the other axial direction. The acoustic ridges 178,180 represent the concentration of a stochastic parameter that propagates through the flow 108 and is a mathematical manifestation of the relationship between the spatial variations and temporal variations described above. Such a plot will indicate a tendency for k-ω pairs to appear more or less along a line 178,180 with some slope, wherein the slope indicates the speed of sound.

The power in the k-ω plane so determined is then provided to an acoustic ridge identifier 182, which uses one or another feature extraction method to determine the location and orientation (slope) of any acoustic ridge present in the left and right k-ω plane. The velocity may be determined by using the slope of one of the two acoustic ridges 178,180 or by averaging the slopes of the acoustic ridges 178,180.

Finally, information including the acoustic ridge orientation (slope) is used by an analyzer 184 to determine the flow parameters relating to measured speed of sound, such as the consistency or composition of the flow, the density of the flow, the average size of particles in the flow, the air/mass ratio of the flow, gas void fraction of the flow, the speed of sound propagating through the flow, and/or the percentage of entrained air within the flow 108.

The array processor 176 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by k=2π/λ where λ is the wavelength of a spectral component, and corresponding angular frequencies given by ω=2πν.

One such technique of determining the speed of sound propagating through the flow 108 is using array processing techniques to define an acoustic ridge 178,180 in the k-ω plane as shown in FIG. 10. The slope of the acoustic ridge 178,180 is indicative of the speed of sound propagating through the flow 108. The speed of sound (SOS) is determined by applying sonar arraying processing techniques to determine the speed at which the one dimensional acoustic waves propagate past the axial array of unsteady pressure measurements distributed along the pipe 110.

The apparatus 100 of the present invention measures the speed of sound (SOS) of one-dimensional sound waves propagating through the mixture 108 to determine the gas void fraction of the mixture 108. It is known that sound propagates through various mediums at various speeds in such fields as SONAR and RADAR fields. The speed of sound propagating through the pipe and flow 12 may be determined using a number of known techniques, such as those set forth in U.S. Pat. Nos. 6,354,147; 6,587,798; 6,732,575; 7,146,864; and 7,062,976, each of which are incorporated herein by reference in their entireties.

While the sonar-based flow meter using an array of sensors 124-130 to measure the speed of sound of an acoustic wave propagating through the mixture 108 is shown and described, one will appreciate that any means for measuring the speed of sound of the acoustic wave may used to determine the entrained gas void fraction of the mixture/fluid or other characteristics of the flow described hereinbefore.

The analyzer 184 of the processing unit 106 provides output signals indicative of characteristics of the process flow 108 that are related to the measured speed of sound (SOS) propagating through the flow 108. For example, to determine the gas void fraction (or phase fraction), the analyzer 184 assumes a nearly isothermal condition for the flow 108. As such the gas void fraction or the void fraction is related to the speed of sound by the following quadratic equation:

$$Ax^2+Bx+C=0, \qquad \text{Eqn. (17)}$$

wherein x is the speed of sound, $A=1+rg/rl*(K_{eff}/P-1)-K_{eff}/P$, $B=K_{eff}/P-2+rg/rl$; $C=1-K_{eff}/rl*a_{meas}^2$); Rg=gas density, rl=liquid density, $K^{eff}$=effective K (modulus of the liquid and pipewall), P=pressure, and $a_{meas}$=measured speed of sound. Effectively, the Gas void fraction may be given by:

$$GVF=(-B+\mathrm{sqrt}(B^2-4*A*C))/(2*A), \qquad \text{Eqn. (18)}$$

Alternatively, the sound speed of a mixture can be related to volumetric phase fraction ($\phi_i$) of the components and the sound speed (a) and densities (ρ) of the component through the Wood equation, $$\frac{1}{\rho_{mix}a_{mix\infty}^2} = \sum_{i=1}^{N} \frac{\phi_i}{\rho_i a_i^2}, \qquad \text{Eqn. (19)}$$

where, $$\rho_{mix} = \sum_{i=1}^{N} \rho_i\phi_i. \qquad \text{Eqn. (20)}$$

One dimensional compression waves propagating within a flow 108 contained within a pipe 110 exert an unsteady internal pressure loading on the pipe 110. The degree to which the pipe 110 displaces as a result of the unsteady pressure loading influences the speed of propagation of the compression wave. The relationship among the infinite domain speed of sound and density of a mixture; the elastic modulus (E), thickness (t), and radius (R) of a vacuum-backed cylindrical conduit; and the effective propagation velocity ($a_{eff}$) for one dimensional compression is given by the following expression:

$$a_{eff} = \frac{1}{\sqrt{1/a_{mix\infty}^2 + \rho_{mix}\frac{2R}{Et}}}. \qquad \text{Eqn. (21)}$$

Figure 11:
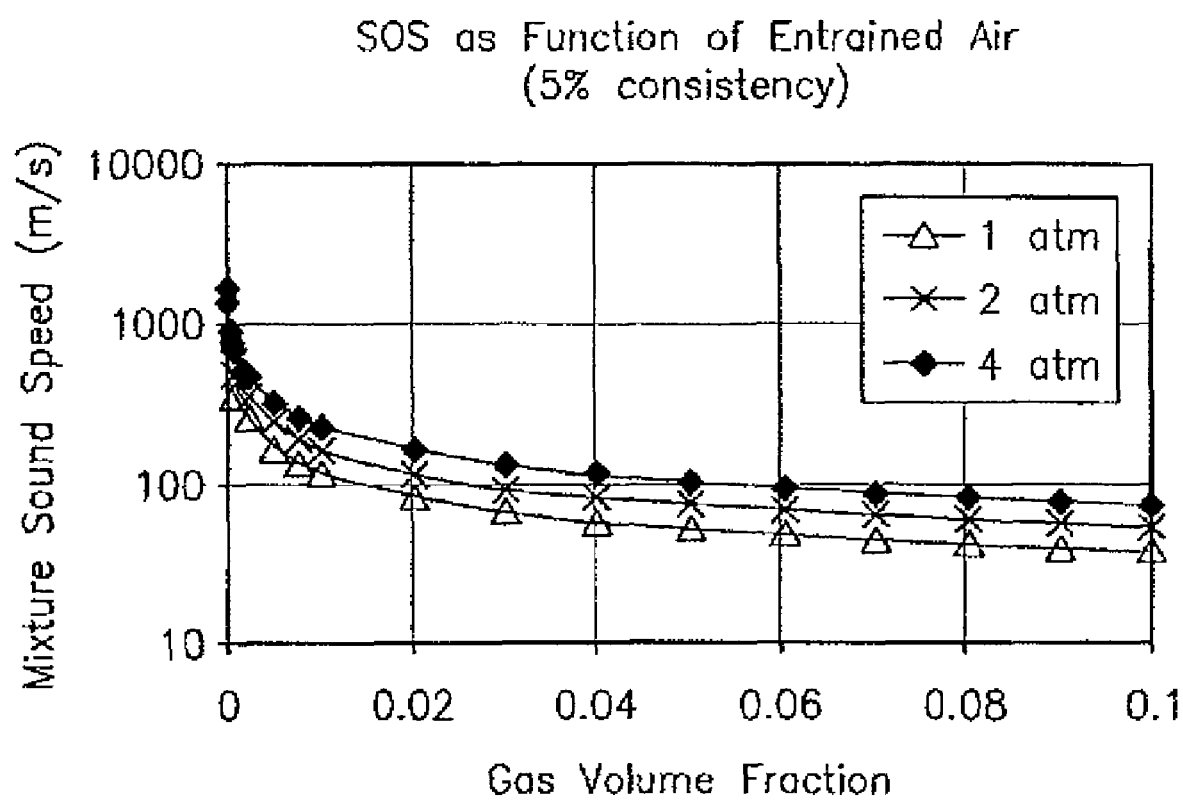
FIG. 11 is a k-ω plot of data processed from an array of pressure sensors use to measure the speed of sound of a fluid flow passing in a pipe, in accordance with the present invention.

The mixing rule essentially states that the compressibility of a mixture ($1/(\rho a^2)$) is the volumetrically-weighted average of the compressibilities of the components. For gas/liquid mixtures at pressure and temperatures typical of the paper and pulp industry, the compressibility of gas phase is orders of magnitudes greater than that of the liquid phase. Thus, the compressibility of the gas phase and the density of the liquid phase primarily determine mixture sound speed, and as such, it is necessary to have a good estimate of process pressure to interpret mixture sound speed in terms of volumetric fraction of entrained gas. The effect of process pressure on the relationship between sound speed and entrained air volume fraction is shown in FIG. 11.

It should be appreciated that some or all of the functions within the processing unit 106 may be implemented in software (using a microprocessor or computer) and/or firmware, or may be implemented using analog and/or digital hardware, having sufficient memory, interfaces, and capacity to perform the functions described herein. Moreover, while the embodiments of the present invention disclosed herein show the pressure sensors 124-130 disposed on the pipe 110, separate from the density meter 102, the present invention contemplates that the sonar meter 104 may be integrated with the density meter 102 to thereby provide a single apparatus. In this integrated embodiment, the pressure sensors 124-130 may be disposed on one or both of the tubes of the density meter 102.

Figure 12:
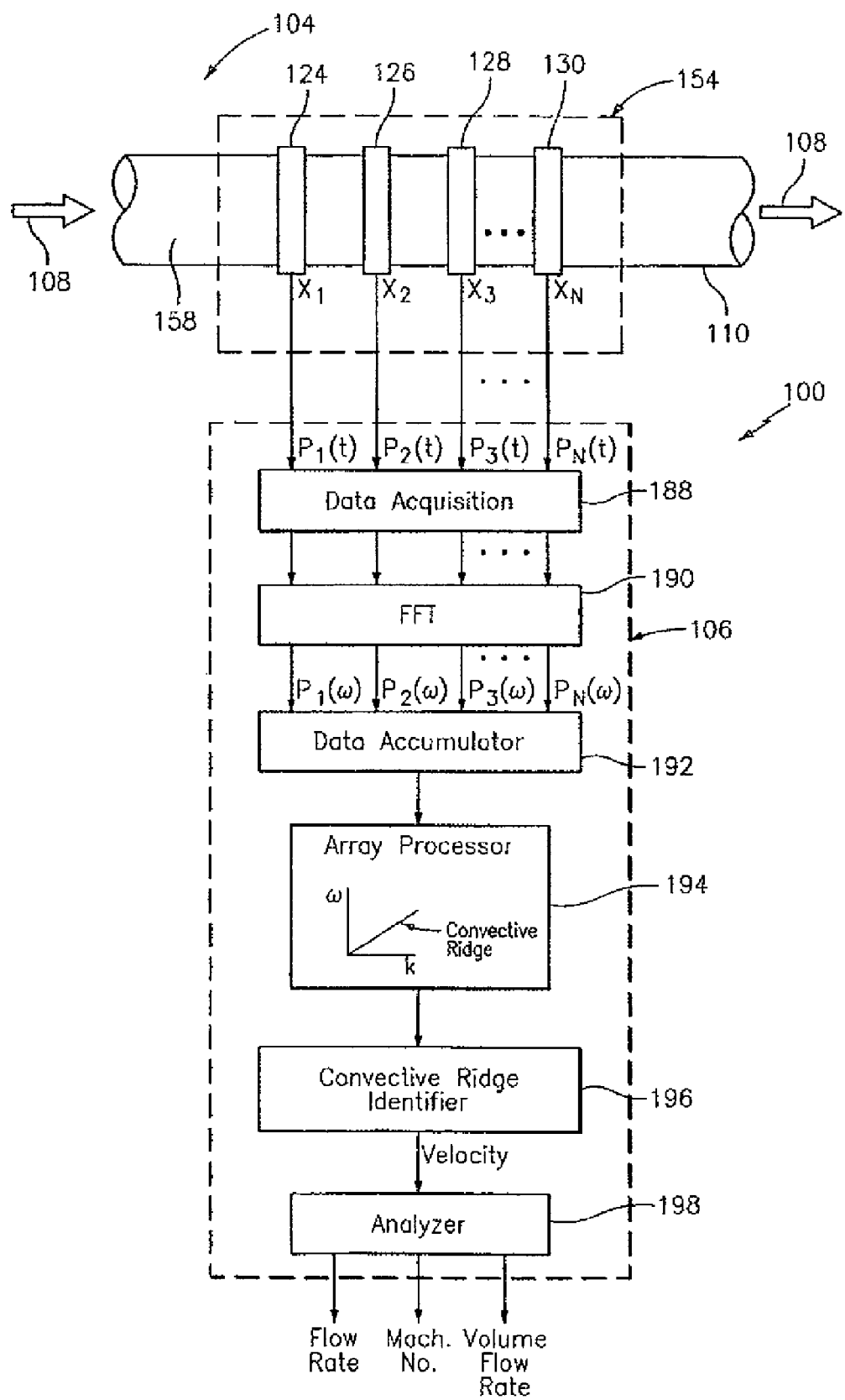
FIG. 12 is a schematic block diagram of a volumetric flow meter having an array of sensor, in accordance with the present invention.
Figure 13:
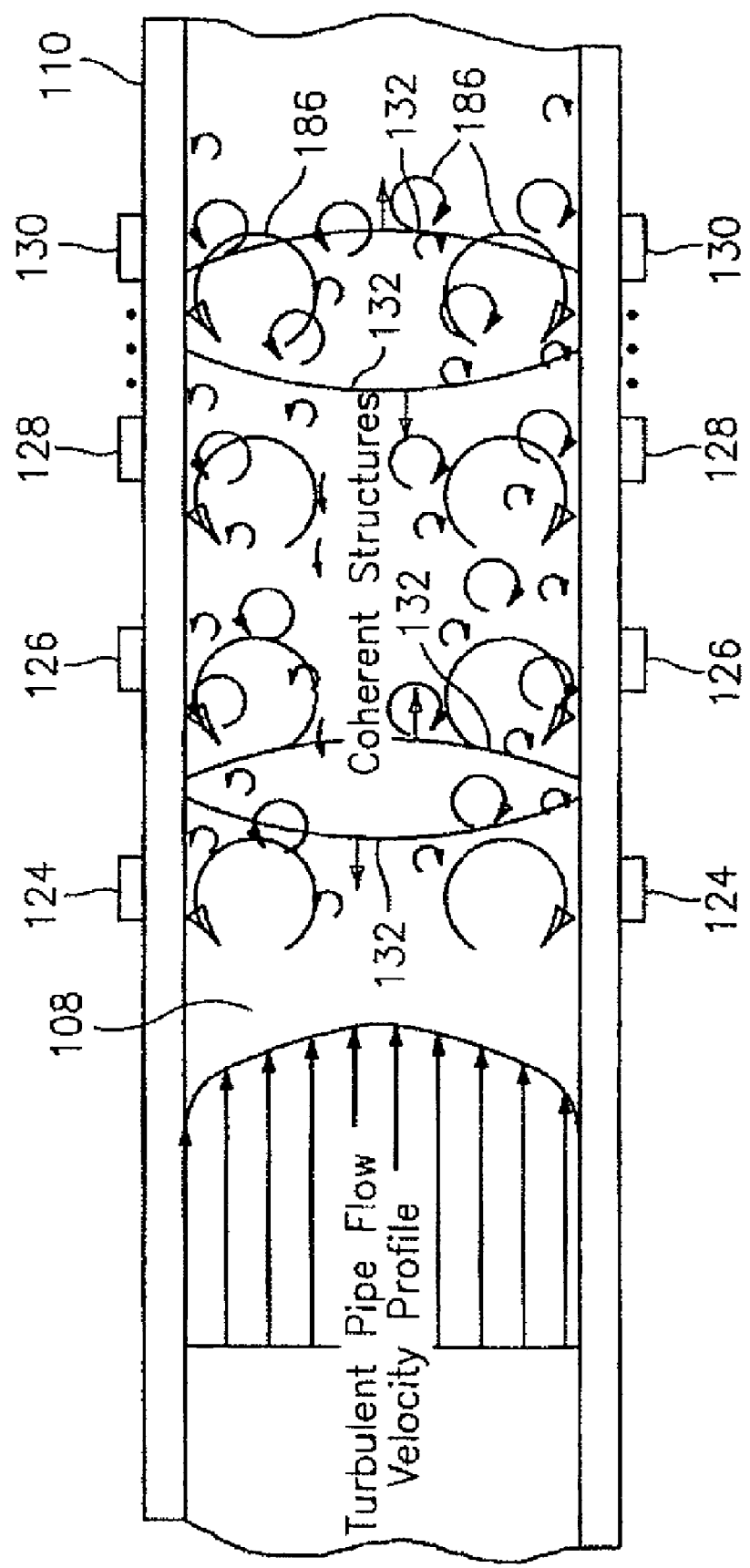
FIG. 13 is a graphical cross-sectional view of the fluid flow propagating through a pipe, in accordance with the present invention.

As shown in FIG. 12 and FIG. 13, the sonar meter 104 may process the array of pressure signals to determine the velocity and/or the volumetric flow of fluid flow 108. The sonar meter 104 embodying the present invention has an array of at least two pressure sensors 124,126 located at two locations $x_1, x_2$ axially along the pipe 110 for sensing respective stochastic signals propagating between the sensors 124,126 within the pipe 110 at their respective locations. Each sensor 124,126 provides a signal indicating an unsteady pressure at the location of each sensor 124, 126 at each instant in a series of sampling instants. One will appreciate that the sensor array 124-130 may include more than two pressure sensors as depicted by pressure sensor 128,130 at location $x_3, x_N$. The pressure generated by the convective pressure disturbances (e.g., eddies 186, see FIG. 13) may be measured through strained-based sensors and/or pressure sensors 124-130. The pressure sensors 124-130 provide analog pressure time-varying signals $P_1(t), P_2(t), P_3(t), P_N(t)$ to the signal processing unit 106. The processing unit 106 processes the pressure signals to first provide output signals indicative of the pressure disturbances that convect with the flow 108, and subsequently, provide output signals in response to pressure disturbances generated by convective waves propagating through the flow 108, such as velocity, Mach number and volumetric flow rate of the process flow 108.

The processing unit 106 receives the pressure signals from the array of sensors 124-130. A data acquisition unit 188 (e.g., A/D converter) converts the analog signals to respective digital signals. The FFT logic 190 calculates the Fourier transform of the digitized time-based input signals $P_1(t)$-$P_N(t)$ and provides complex frequency domain (or frequency based) signals $P_1(\omega), P_2(\omega), P_3(\omega), P_N(\omega)$ indicative of the frequency content of the input signals. Instead of FFT's, any other technique for obtaining the frequency domain characteristics of the signals $P_1(t)$-$P_N(t)$, may be used. For example, the cross-spectral density and the power spectral density may be used to form a frequency domain transfer functions (or frequency response or ratios) discussed hereinafter.

One technique of determining the convection velocity of the turbulent eddies 186 within the process flow 108 is by characterizing a convective ridge of the resulting unsteady pressures using an array of sensors or other beam forming techniques, similar to that described in U.S. Pat. Nos. 6,889,562 and 6,609,069, which are incorporated herein by reference in their entireties.

Figure 14:
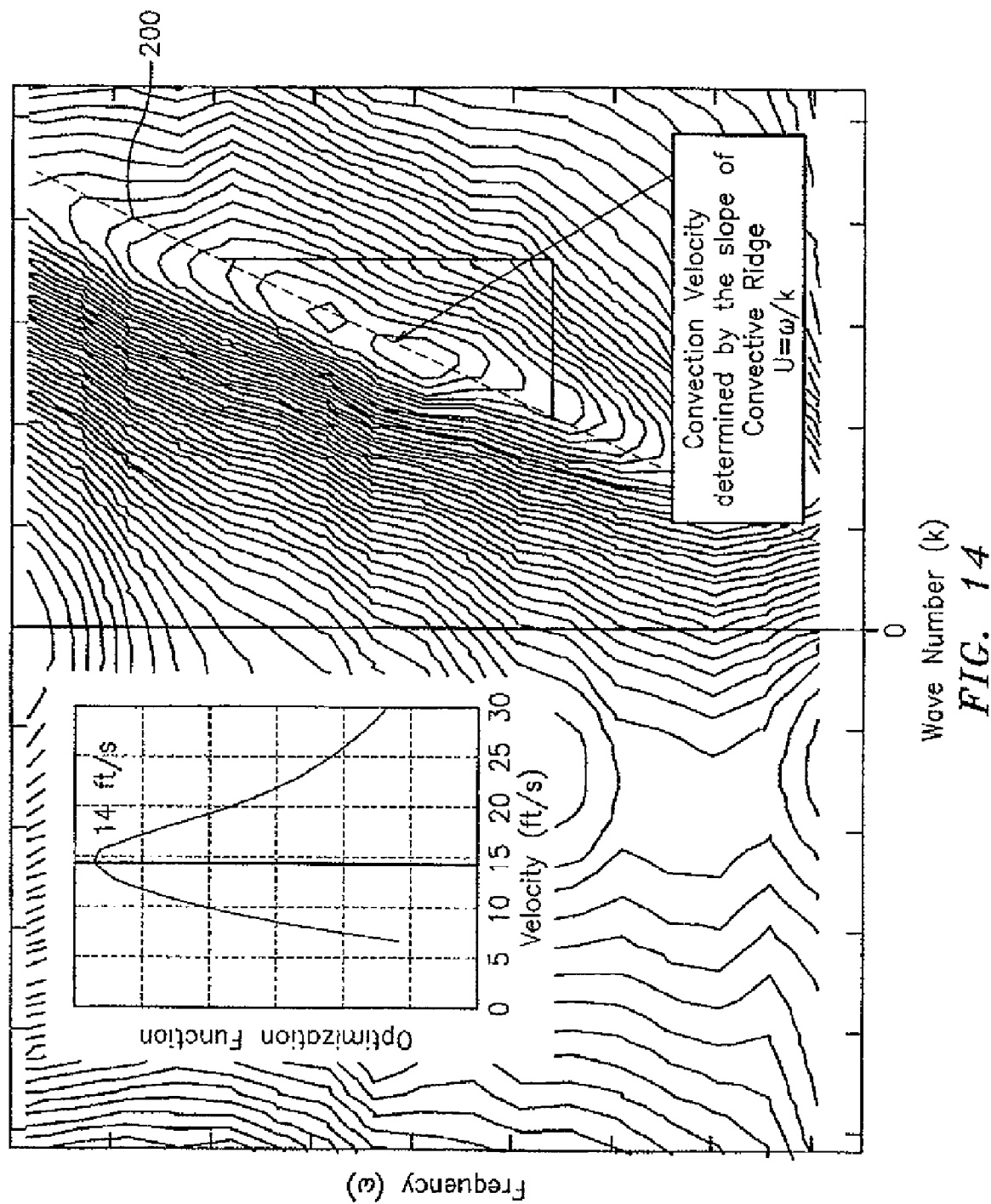
FIG. 14 is a k-ω plot of data processed from an array of pressure sensors use to measure the velocity of a fluid flow passing in a pipe, in accordance with the present invention.

A data accumulator 192 accumulates the frequency signals $P_1(\omega)$-$P_N(\omega)$ over a sampling interval, and provides the data to an array processor 194, which performs a spatial-temporal (two-dimensional) transform of the sensor data, from the xt domain to the k-ω domain, and then calculates the power in the k-ω plane, as represented by a k-ω plot (See FIG. 14).

The array processor 194 uses standard so-called beam forming, array processing, or adaptive array-processing algorithms, i.e. algorithms for processing the sensor signals using various delays and weighting to create suitable phase relationships between the signals provided by the different sensors, thereby creating phased antenna array functionality. In other words, the beam forming or array processing algorithms transform the time domain signals from the sensor array into their spatial and temporal frequency components, i.e. into a set of wave numbers given by $k=2\pi/\lambda$ where $\lambda$ is the wavelength of a spectral component, and corresponding angular frequencies given by $\omega=2\lambda\nu$.

It should be appreciated that the prior art teaches many algorithms of use in spatially and temporally decomposing a signal from a phased array of sensors, and the present invention is not restricted to any particular algorithm. One particular adaptive array processing algorithm is the Capon method/algorithm. While the Capon method is described as one method, the present invention contemplates the use of other adaptive array processing algorithms, such as MUSIC algorithm. The present invention recognizes that such techniques can be used to determine flow rate, i.e. that the signals caused by a stochastic parameter convecting with a flow are time stationary and have a coherence length long enough that it is practical to locate sensor units apart from each other and yet still be within the coherence length.

Convective characteristics or parameters have a dispersion relationship that can be approximated by the straight-line equation, $$k=\omega/u,\qquad\text{Eqn. (22)}$$

where u is the convection velocity (flow velocity). A plot of k-ω pairs obtained from a spectral analysis of sensor samples associated with convective parameters portrayed so that the energy of the disturbance spectrally corresponding to pairings that might be described as a substantially straight ridge, a ridge that in turbulent boundary layer theory is called a convective ridge. What is being sensed are not discrete events of turbulent eddies, but rather a continuum of possibly overlapping events forming a temporally stationary, essentially white process over the frequency range of interest. In other words, the convective eddies 186 are distributed over a range of length scales and hence temporal frequencies.

To calculate the power in the k-ω plane, as represented by a k-ω plot (see FIG. 14) of either of the signals, the array processor 194 determines the wavelength and so the (spatial) wavenumber k, and also the (temporal) frequency and so the angular frequency ω, of various of the spectral components of the stochastic parameter. There are numerous algorithms available in the public domain to perform the spatial/temporal decomposition of arrays of sensor units 124-130.

It should be appreciated that the present invention may use temporal and spatial filtering to precondition the signals to effectively filter out the common mode characteristics and other long wavelength (compared to the sensor spacing) characteristics in the pipe 110 by differencing adjacent sensors and retain a substantial portion of the stochastic parameter associated with the flow field and any other short wavelength (compared to the sensor spacing) low frequency stochastic parameters.

In the case of suitable turbulent eddies 186 (see FIG. 13) being present, the power in the k-ω plane shown in a k-ω plot of FIG. 14 shows a convective ridge 200. The convective ridge 200 represents the concentration of a stochastic parameter that convects with the flow 108 and is a mathematical manifestation of the relationship between the spatial variations and temporal variations described above. Such a plot will indicate a tendency for k-ω pairs to appear more or less along a line 200 with some slope, wherein the slope indicates the flow velocity.

Once the power in the k-ω plane is determined, a convective ridge identifier 196 uses one or another feature extraction method to determine the location and orientation (slope) of any convective ridge 200 present in the k-ω plane. In one embodiment, a so-called slant stacking method is used, a method in which the accumulated frequency of k-ω pairs in the k-ω plot along different rays emanating from the origin are compared, each different ray being associated with a different trial convection velocity (in that the slope of a ray is assumed to be the flow velocity or correlated to the flow velocity in a known way). The convective ridge identifier 196 provides information about the different trial convection velocities, information referred to generally as convective ridge information.

The analyzer 198 examines the convective ridge information including the convective ridge orientation (slope). Assuming the straight-line dispersion relation given by $k=\omega/u$, the analyzer 198 determines the flow velocity, Mach number and/or volumetric flow. The volumetric flow is determined by multiplying the cross-sectional area of the inside of the pipe with the velocity of the process flow 108.

For any embodiments described herein, the pressure sensors 124-130, including electrical strain gages, optical fibers and/or gratings among others as described herein, may be attached to the pipe by adhesive, glue, epoxy, tape or other suitable attachment means to ensure suitable contact between the sensor and the pipe. The sensors 124-130 may alternatively be removable or permanently attached via known mechanical techniques such as mechanical fastener, spring loaded, clamped, clam shell arrangement, strapping or other equivalents. Alternatively, the strain gages, including optical fibers and/or gratings, may be embedded in a composite pipe. If desired, for certain applications, the gratings may be detached from (or strain or acoustically isolated from) the pipe if desired.

It is also within the scope of the present invention that any other strain sensing technique may be used to measure the variations in strain in the pipe 110, such as highly sensitive piezoelectric, electronic or electric, strain gages attached to or embedded in the pipe. Accelerometers may be also used to measure the unsteady pressures. Also, other pressure sensors 124-130 may be used, as described in a number of the aforementioned patents, which are incorporated herein by reference in their entireties. In another embodiment, the sensor may comprise of piezofilm or strips (e.g. PVDF) as described in at least one of the aforementioned patent applications, which are incorporated herein by reference in their entireties.

While the illustrations show four sensors mounted or integrated in a tube of the coriolis meter, the invention contemplates any number of sensors in the array as taught in at least one of the aforementioned patent applications. Also the invention contemplates that the array of sensors 124-130 may be mounted or integrated with a tube of a coriolis meter having shape, such as pretzel shape, U-shaped (as shown), straight tube and any curved shape. The invention further contemplated providing an elongated, non-vibrating (or oscillating) portion that permits a greater number of sensors to be used in the array.

While the present invention describes an array of sensors for measuring the speed of sound propagating through the flow for use in interpreting the relationship between coriolis forces and the mass flow through a coriolis meter. Several other methods exists and may also be used, individually or in a combined manner. For example, for a limited range of fluids, an ultrasonic device could be used to determine speed of sound of the fluid entering. It should be noted that the theory indicates that the interpretation of coriolis meters will be improved for all fluids if the sound speed of the process fluid is measured and used in the interpretation. Thus, knowing that the sound speed of the fluid is 5000 ft/sec as it would be for a water like substance, compared to 1500 ft/sec as it would be for say supercritical ethylene, would improve the performance of a coriolis based flow and density measurement. These measurements could be performed practically using existing ultrasonic meters.

Another approach to determine speed of sound of the fluids is to measure the resonant frequency of the acoustic modes of the flow tubes. When installed in a flow line, the cross sectional area changes associated with the transition from the pipe into the typically much smaller flow tubes creates a significant change in acoustic impedance. As a result of this change in impedance, the flow tube acts as somewhat of a resonant cavity. By tracking the resonant frequency of this cavity, one could determine the speed of sound of the fluid occupying the cavity. This could be performed with a single pressure sensitive device, mounted either on the coriolis meter, or on the piping network attached to the coriolis meter.

In a more general aspect, the present invention contemplates the ability of augmenting the performance of a coriolis meter using any method or means for measuring the gas void fraction of the fluid flow.

In one embodiment of the present invention, as shown in FIG. 13, each of the pressure sensors 124-130 may include a piezoelectric film sensor to measure the unsteady pressures of the fluid flow 108 using either technique described hereinbefore. The piezoelectric film sensors include a piezoelectric material or film to generate an electrical signal proportional to the degree that the material is mechanically deformed or stressed. The piezoelectric sensing element is typically conformed to allow complete or nearly complete circumferential measurement of induced strain to provide a circumferential-averaged pressure signal. The sensors can be formed from PVDF films, co-polymer films, or flexible PZT sensors, similar to that described in "Piezo Film Sensors Technical Manual" provided by Measurement Specialties, Inc., which is incorporated herein by reference. A piezoelectric film sensor that may be used for the present invention is part number 1-1002405-0, LDT4-028K, manufactured by Measurement Specialties, Inc.

Piezoelectric film ("piezofilm"), like piezoelectric material, is a dynamic material that develops an electrical charge proportional to a change in mechanical stress. Consequently, the piezoelectric material measures the strain induced within the pipe 110 due to unsteady pressure variations (e.g., acoustic waves) within the process mixture 108. Strain within the pipe 110 is transduced to an output voltage or current by the attached piezoelectric sensor. The piezoelectrical material or film may be formed of a polymer, such as polarized fluoropolymer, polyvinylidene fluoride (PVDF). The piezoelectric film sensors are similar to that described in U.S. patent application Ser. No. 10/712,818, U.S. patent application Ser. No. 10/712,833, and U.S. Pat. No. 7,146,864, which are incorporated herein by reference in their entireties.

Another embodiment of the present invention includes pressure sensors such as pipe strain sensors, accelerometers, velocity sensors or displacement sensors, discussed hereinafter, that are mounted onto a strap to enable the pressure sensor to be clamped onto the pipe 110. The sensors may be removable or permanently attached via known mechanical techniques such as mechanical fastener, spring loaded, clamped, clam shell arrangement, strapping or other equivalents. These certain types of pressure sensors, it may be desirable for the pipe 110 to exhibit a certain amount of pipe compliance.

Instead of single point pressure sensors 124-130, at the axial locations along the pipe 110, two or more pressure sensors may be used around the circumference of the pipe 110 at each of the axial locations. The signals from the pressure sensors around the circumference at a given axial location may be averaged to provide a cross-sectional (or circumference) averaged unsteady acoustic pressure measurement. Other numbers of acoustic pressure sensors and annular spacing may also be used. It should be appreciated that averaging multiple annular pressure sensors reduces noises from disturbances and pipe vibrations and other sources of noise not related to the one-dimensional acoustic pressure waves in the pipe 110, thereby creating a spatial array of pressure sensors to help characterize the one-dimensional sound field within the pipe 110.

The pressure sensors 124-130 described herein may be any type of pressure sensor, capable of measuring the unsteady (or ac or dynamic) pressures within a pipe 110, such as piezoelectric, optical, capacitive, resistive (e.g., Wheatstone bridge), accelerometers (or geophones), velocity measuring devices, displacement measuring devices, etc. If optical pressure sensors are used, the sensors 124-130 may be Bragg grating based pressure sensors, such as that described in U.S. Pat. No. 6,016,702, and in U.S. Pat. No. 6,959,604, which are incorporated herein by reference in their entireties. In an embodiment of the present invention that utilizes fiber optics as the pressure sensors, they may be connected individually or may be multiplexed along one or more optical fibers using wavelength division multiplexing (WDM), time division multiplexing (TDM), or any other optical multiplexing techniques.

In certain embodiments of the present invention, a piezoelectronic pressure transducer may be used as one or more of the pressure sensors 124-130 and it may measure the unsteady (or dynamic or ac) pressure variations inside the pipe or tube 10 by measuring the pressure levels inside of the tube 10. These sensors may be ported within the pipe 110 to make direct contact with the mixture 108. In an embodiment of the present invention, the sensors comprise pressure sensors manufactured by PCB Piezotronics. In one pressure sensor there are integrated circuit piezoelectric voltage mode-type sensors that feature built-in microelectronic amplifiers, and convert the high-impedance charge into a low-impedance voltage output. Specifically, a Model 106B manufactured by PCB Piezotronics is used which is a high sensitivity, acceleration compensated integrated circuit piezoelectric quartz pressure sensor suitable for measuring low pressure acoustic phenomena in hydraulic and pneumatic systems. It has the unique capability to measure small pressure changes of less than 0.001 psi under high static conditions. The Model 106B has a 300 mV/psi sensitivity and a resolution of 91 dB (0.0001 psi).

The pressure sensors incorporate a built-in MOSFET microelectronic amplifier to convert the high-impedance charge output into a low-impedance voltage signal. The sensor is powered from a constant-current source and can operate over long coaxial or ribbon cable without signal degradation. The low-impedance voltage signal is not affected by triboelectric cable noise or insulation resistance-degrading contaminants. Power to operate integrated circuit piezoelectric sensors generally takes the form of a low-cost, 24 to 27 VDC, 2 to 20 mA constant-current supply. A data acquisition system of the present invention may incorporate constant-current power for directly powering integrated circuit piezoelectric sensors.

Most piezoelectric pressure sensors are constructed with either compression mode quartz crystals preloaded in a rigid housing, or unconstrained tourmaline crystals. These designs give the sensors microsecond response times and resonant frequencies in the hundreds of kHz, with minimal overshoot or ringing. Small diaphragm diameters ensure spatial resolution of narrow shock waves. The output characteristic of piezoelectric pressure sensor systems is that of an AC-coupled system, where repetitive signals decay until there is an equal area above and below the original base line. As magnitude levels of the monitored event fluctuate, the output remains stabilized around the base line with the positive and negative areas of the curve remaining equal.

It is also considered within the scope of the present invention that any strain sensing technique may be used to measure the variations in strain in the pipe, such as highly sensitive piezoelectric, electronic or electric, strain gages and piezo-resistive strain gages attached to the pipe 110. Other strain gages include resistive foil type gages having a race track configuration similar to that disclosed U.S. Pat. No. 6,354,147, which is incorporated herein by reference. The invention also contemplates strain gages being disposed about a predetermined portion of the circumference of pipe 110. The axial placement of and separation distance $\Delta X_1$, $\Delta X_2$ between the strain sensors are determined as described herein above.

The water cut of a liquid continuous mixture within a pipe can be determined by measuring the speed of sound of the mixture. The speed of sound of a two phase mixture can be related to the volumetric phase fraction of the mixture through the Wood's equation:

$$\frac{1}{\rho_{mix} a_{mix}^2} = \frac{\phi_{oil}}{\rho_{oil} a_{oil}^2} + \frac{\phi_w}{\rho_w a_w^2}$$

$$\rho_{mix} = \rho_{oil}\phi_{oil} + \rho_w \phi_w$$

It is preferred to use a pair of normal incident ultrasonic transducers to measure the speed of sound of the mixture. The transducers may be placed at the 3 o'clock and 9 o'clock orientation on a horizontal or near horizontal flow line. The transducers should produce a signal at a frequency high enough (e.g., 500 KHz transducers) such that the transit time of the ultrasonic pulse traversing the pipe is not significantly impacted by the presence of entrained gases in the liquid continuous mixture.

The graph shown in FIG. 16 illustrates the impact of entrained gases on 1) the speed of sound measured by a pair of ultrasonic sensors; and on 2) a passive SONAR system measuring relatively low frequency sound. The data line representing the speed of sound values determined by the ultrasonic sensors is essentially independent of the amount of entrained gases within the liquid. In contrast, the speed of sound values determined by the passive SONAR system are significantly affected by the amount of entrained gas within the liquid.

For a clamp-on device operable to determine the water cut of a fluid flow, there are several factors that must be considered relating to the operation of the device. First, the intermittent nature of slugs traveling within the flow, and the associated level of non-stationarity to the water cut measurement, must be considered. The intermittent nature of the slugs can be addressed by continuously measuring the ultrasonic transit time, with the speed of sound of the mixture being determined only when the received fluid borne component is determined to be within acceptable limits and of sufficient quality to be deemed valid.

Second, it is likely that the slugs of liquid traveling within the fluid flow will contain some entrained gases. Although the entrained gases may not have any first order impact on the propagation velocity of sufficiently high frequency ultrasonic waves, the entrained gases may in general increase attenuation of the ultrasonic signals while propagating through the fluid, impeding accurate characterization of the fluid born arrival times. To accommodate such attenuation, quadrature techniques may be used to determine the fluid arrival time.

Third, it is also recognized that the structural borne component of the ultrasonic signal measured at the receiving transducer will serve to mask the fluid borne component. Therefore, to enhance the ability of a clamp-on, normal incident ultrasonic water cut measurement, it is proposed herein to use a structurally tailored housing to either modify the ultrasonic vibrational characteristics of the pipe, or to add a structure or other mechanism that operates to damp any structural borne component within the pipe, and thereby improve the ability of the device to accurately determine the fluid borne component and thus fluid sound speed. Examples of structurally significant housings operable to modify structural borne components or to damp them, include those described in U.S. patent application Ser. No. 11/926,757 filed Oct. 29, 2007, and U.S. patent application Ser. No. 11/881,477 filed Jul. 27, 2007, both of which are hereby incorporated by reference in their entirety. Examples of structurally significant housings include housings with increased thickness walls, housings with viscoelastic materials disposed between plates, piezoelectric materials, etc. Whether the structural borne component is modified into a benign form or damped, the ability of the transmitting and receiving transducers of the ultrasonic sensor to send and receive an ultrasonic signal through the fluid is enhanced by minimizing the adverse effects of the structurally borne component of the ultrasonic signal.

Fourth, it is envisioned that, while the slug is present, the transient time measurement of the ultrasonic signal will be similar to that of a pipe with liquid continuous flow. During this period, the fluid borne component of the ultrasonic signal will be modulated by coherent structures within the flow field. Under ideal circumstances, the structural borne component of the signal will be largely stationary. To address both the fluid and structural borne components of the signal, however, relatively minor changes in the phase and amplitude of the fluid borne component can be isolated to distinguish the fluid borne components from the more stationary structural borne components to enable a mean arrival time determination.

For fluid flows (having liquid and gas components) exhibiting slugging phenomenon, the region between two sensors will be filled with gas/liquid mixtures ranging from gas continuous regimes to liquid continuous regimes. As stated earlier, a slug is present within a pipe at a given location when a liquid component body fills substantially all of the cross-sectional area of the pipe at the location. The presence of a liquid slug (including a liquid continuous regime) versus a gas component body (included a gas continuous regime) can be clearly differentiated by significantly different transit times for an ultrasonic signal sent through the fluid. The transit time for an ultrasonic signal to propagate across a pipe is given nominally by:

$$\Delta T = \frac{D}{a}$$

where "D" represents the pipe diameter and "a" represents the speed of sound of the mixture. Representative values for oil, water, and gas sound speeds and times required to propagate across a four (4) inch diameter pipe are given below.

| Component | SOS (ft/sec) | Diameter (in) | ΔT (micro Seconds) |
|---|---|---|---|
| Oil | 4000 | 4 | 83.3 |
| Water | 5000 | 4 | 66.7 |
| Methane | 1200 | 4 | 277.8 |

For oil industry applications, when a liquid component body fills substantially all of the cross-sectional area of the pipe at a location aligned with the ultrasonic sensor (i.e., when a slug is present), the transit time of the fluid borne signal should be somewhere between the transit time through a pure water phase (i.e., about 66.7 micro seconds) for a four inch diameter pipe, and the transit time through pure oil phase (i.e., about 83.3 micro seconds) for the same size pipe. For gas continuous situations (i.e., no slug present) there will likely be no discernable fluid borne signal arrival within the time window described above. In this example, with pure methane in the pipe, the fluid borne signal would arrive at 278 microseconds; i.e., 4 to 5 times later than a liquid continuous pulse. Consequently, the fluid phase within the pipe can readily be determined.

If the slugging characteristics of the flow within the existing piping system are insufficient to generate the desired and/or necessary slugging characteristic to permit the determination of a fluid characteristic (e.g., speed of sound, water cut, etc.), the piping can be modified to promote slugging behavior. Our current understanding is that a piping configuration that includes a flow impedance, such as a directional change, will promote slugging formation. The slug generating pipe section is positioned in the piping system so that the liquid component slugs created by the pipe section can be used by the clamp-on water cut metering device or other flow measuring device; i.e., the slug generator section can be positioned upstream, at or adjacent the measuring device. FIG. 17 shows a schematic depiction of a section of piping (e.g., an "inverted U-tube") arranged to facilitate the formation of slugs. Flow is left to right. The slug generator integrated with a differential pressure measurement (i.e., P1, P2) and a SONAR meter (preferable an active meter for mixture velocity and for water cut measurement) can be used as a minimally intrusive three-phase flow meter. The term "active" is used herein to reflect a device that emits a signal into a fluid flow to gather information; e.g., an ultrasonic transducer. FIG. 18 schematically illustrates another piping configuration that could be used to facilitate slug formation. In this embodiment, the piping includes divergent sections that collectively form a triangular-shaped piping configuration, with a SONAR meter disposed near the intersection of two of the sharp turn "elbow" of the configuration, and a differential pressure measurement (i.e., P1, P2) across the configuration. The configurations shown in FIGS. 17 and 18 are examples of acceptable configurations, and the present invention is not limited to such configurations. As indicated above, the "slug generator" piping section may be arranged with one or more of a differential pressure measurement device, an ultrasonic transducer, and a SONAR meter to create, for example, a three-phase flow meter. It is not required, however, that the slug generator piping section be located with any of the aforesaid devices. Piping configurations designed to facilitate slug formation in the process flow provide the advantage of expanding the range of input conditions over which a clamp-on water cut metering device can be used to leverage the naturally occurring slugging behavior.

Figure 19:
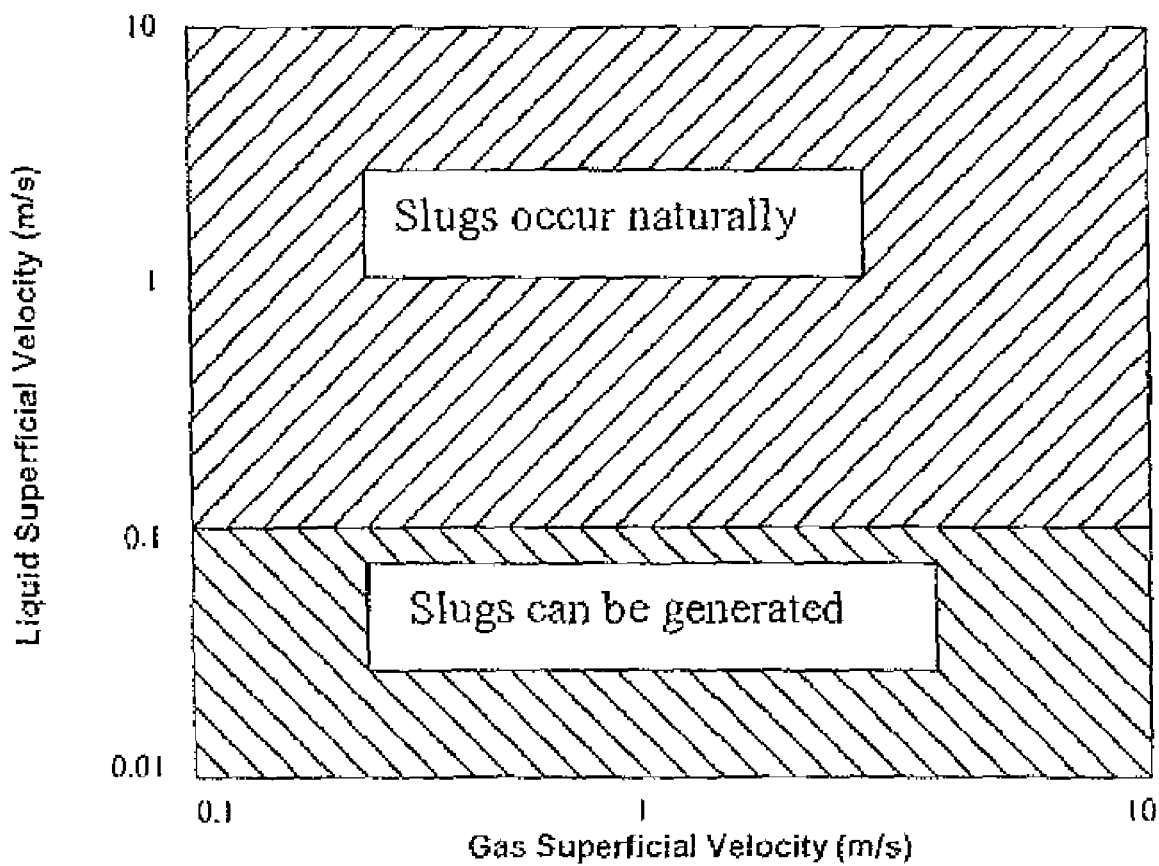
FIG. 19 is a graph of Liquid Superficial Velocity versus Gas Superficial Velocity, illustrating regions of slug formation within a process flow.

FIG. 19 shows a simplified flow regime diagram for a horizontal pipe. As shown, slugging naturally occurs within the fluid flow over wide range of conditions. Depending upon the specific characteristics of the fluid, however, there is likely a liquid superficial velocity value below which slugging is less likely to occur naturally. In that region, slugs can be induced within the fluid flow via appropriate piping modification, and thereby increase the range of conditions over which slugging can be utilized.

It should appreciated that while the present invention disclosed herein is shown as being used when the fluid 108 flowing within the pipe 110 is slugging, i.e. not filling the entire pipe 110, the present invention may also be used when the pipe is primarily full. Also, it should be appreciated that the flow velocity $U_{mix}$ of the fluid and/or density of the fluid $\rho_{mix}$ can be measured with or without a full pipe 110 as illustrated in FIGS. 3b, 5 and 7. Moreover, while a number of preferred embodiments have been described herein, any combination of the features described herein may be used. It should be understood that, unless stated otherwise herein, any of the features, characteristics, alternatives or modifications described regarding a particular embodiment herein may also be applied, used, or incorporated with any other embodiment described herein. Also, the drawings herein are not drawn to scale.

Although the invention has been described and illustrated with respect to exemplary embodiments thereof the foregoing and various other additions and omissions may be made therein and thereto without departing from the spirit and scope of the present invention.

What is claimed is:

1. A method for determining at least one characteristic of a fluid flowing within a pipe, wherein the fluid flow includes one or more liquid component bodies and one or more gas component bodies, which bodies occupy a substantial cross-sectional area of the pipe when passing a location in the pipe, the method comprising:
   transmitting a signal into the fluid flow at the location within the pipe, and receiving the signal after it has traversed at least a portion of the fluid flow;
   determining a time of flight of the signal traversing the fluid flow;
   determining the presence of a liquid component body at the location in the pipe, using the determined time of flight;
   determining at least one characteristic of the fluid using fluid data generated only if the liquid component body is present at the location.

2. The method of claim 1, wherein the step of determining the presence of a liquid component body at the location in the pipe comprises comparing the determined time of flight to data related to one or more predetermined time of flight values.

3. The method of claim 2, wherein the data is related to time of flight values within at least one of a liquid hydrocarbon water, and mixtures thereof.

4. The method of claim 1, wherein the step of determining the presence of a liquid component body at the location in the pipe comprises calculating the speed of sound within the fluid using the determined time of flight.

5. The method of claim 4, wherein the step of determining the presence of a liquid component body at the location in the pipe further comprises comparing the calculated speed of sound value to data related to the speed of sound within one or more predetermined liquids.

6. The method of claim 5, wherein the data relates to the speed of sound within one or more liquid hydrocarbons, water, and mixtures thereof.

7. The method of claim 6, wherein the step of transmitting a signal into the fluid flow at the location within the pipe is performed continuously.

8. The method of claim 1, wherein the signal is transmitted through a pipe wall before traversing at least a portion of the fluid flow, and the signal passes through the pipe wall before being received, the method further comprising the step of:
   modifying the pipe at the location to account for a structural borne component of the signal.

9. The method of claim 8, wherein the step of modifying the pipe includes modifying the pipe to damp the structural borne component of the signal.

10. The method of claim 1, wherein the pipe is oriented substantially horizontal at the location, and the signal is transmitted into the fluid flow by a ultrasonic transmitter and received by an ultrasonic receiver, which transmitter and receiver are oriented relative to the pipe such that the signal traverses the fluid flow in a direction that is normal to the fluid flow.

11. The method of claim 10, wherein the transmitter and receiver are aligned along a line that is substantially horizontal and normal to the fluid flow.

12. The method of claim 1, further comprising the step of providing a pipe section that is configured to promote formation of liquid component bodies within the fluid flow.

13. The method of claim 12, wherein the pipe section is positioned adjacent or upstream of the location in the pipe.

14. The method of claim 12, further comprising the steps of:
   measuring a difference in pressure across the pipe section;
   determining a fluid flow velocity and a water cut value within or adjacent the pipe section when a liquid component body is present, wherein one or more of the difference in pressure, fluid flow velocity, and water cut value are used to in the step of determining at least one characteristic of the fluid.

15. The method of claim 14, wherein the steps of determining a fluid flow velocity and a water cut value are performed using an ultrasonic meter.

16. An apparatus for determining at least one characteristic of a fluid flowing within a pipe, which fluid includes one or more liquid component bodies and one or more gas component bodies, which bodies occupy a substantial cross-sectional area of the pipe when passing a location in the pipe, the apparatus comprising:
   a sensor having a transmitter and a receiver, operable to send a signal into the fluid flow at the location within the pipe, receive the signal after it has traversed at least a portion of the fluid flow, and produce sensor data representative of the signal received;
   a processing device in communication with the sensor, which device is operable to determine a time of flight of the signal traversing the fluid using the sensor data and determine a presence of a liquid component body at the location in the pipe using the determined time of flight, and to determine at least one characteristic of the fluid only if the presence of a liquid component body at the location is determined.

17. The apparatus of claim 16, wherein the processing device is operable to determine the presence of a liquid component body at the location in the pipe by comparing the determined time of flight data to data related to one or more predetermined time of flight values.

18. The apparatus of claim 17, wherein the data is related to time of flight values within at least one of a liquid hydrocarbon, water and mixtures thereof.

19. The apparatus of claim 16, wherein the processing device is operable to determine the presence of a liquid component body at the location in the pipe by calculating the speed of sound within the fluid using the determined time of flight.

20. The apparatus of claim 19, wherein the processing device is operable to determine the presence of a liquid component body at the location in the pipe by comparing the calculated speed of sound value to data related to the speed of sound within one or more predetermined liquids.

21. The apparatus of claim 20, wherein the data is related to the speed of sound within one or more liquid hydrocarbons, water, and mixtures thereof.

22. The apparatus of claim 21, wherein the sensor is selectively operable to continuously send a signal into the fluid flow at the location within the pipe.

23. The apparatus of claim 16, further comprising a structurally tailored housing disposed at the location, which structurally tailored housing is operable to modify the pipe at the location in a manner that substantially decreases an affect of a structural borne component of the signal.

24. The apparatus of claim 23, wherein the structurally tailored housing is operable to damp structural borne components of the signal.

25. The apparatus of claim 16, wherein the apparatus is attachable to the pipe in a manner that the signal traveling between the transmitter and the receiver traverses the fluid flow in a direction that is normal to the fluid flow.

26. The apparatus of claim 24, wherein the transmitter and receiver are aligned along a line that is substantially horizontal and normal to the fluid flow.

27. The apparatus of claim 16, further comprising a pipe section configured to promote formation of liquid component bodies within the fluid flow.

28. The apparatus of claim 27, further comprising:
    a pressure difference meter positioned to determine a difference in pressure across the pipe section, which pressure difference meter is in communication with the processing device;
    a flow meter disposed within or adjacent the pipe section, which flow meter is operable to determine a velocity of the fluid flow and a water cut value of the fluid flow, and which flow meter is in communication with the processing device.

29. The apparatus of claim 28, wherein the flow meter comprises an ultrasonic sensor.

30. The apparatus of claim 27, wherein the pipe section is positioned adjacent or upstream of the location of the pipe.

* * * * *